(12) United States Patent
Yang et al.

(10) Patent No.: US 11,944,488 B2
(45) Date of Patent: Apr. 2, 2024

(54) SYSTEMS AND METHODS FOR 3D ULTRASOUND IMAGING OF EXTENDED TARGETS USING INTERCHANGEABLE TRACK STANDS

(71) Applicant: Verathon Inc., Bothell, WA (US)

(72) Inventors: Fuxing Yang, Bothell, WA (US); Jeremiah DeHaan, Kirkland, WA (US)

(73) Assignee: VERATHON INC., Bothell, WA (US)

( * ) Notice: Subject to any disclaimer, the term of this patent is extended or adjusted under 35 U.S.C. 154(b) by 101 days.

(21) Appl. No.: 17/171,348

(22) Filed: Feb. 9, 2021

(65) Prior Publication Data
US 2021/0259662 A1     Aug. 26, 2021

Related U.S. Application Data

(60) Provisional application No. 62/980,514, filed on Feb. 24, 2020.

(51) Int. Cl.
*A61B 8/08*     (2006.01)
*A61B 8/00*     (2006.01)
(Continued)

(52) U.S. Cl.
CPC .............. *A61B 8/0891* (2013.01); *A61B 8/14* (2013.01); *A61B 8/4209* (2013.01); *A61B 8/4245* (2013.01); *A61B 8/466* (2013.01); *A61B 8/467* (2013.01); *A61B 8/54* (2013.01); *G06T 7/10* (2017.01); *G06T 7/62* (2017.01);
(Continued)

(58) Field of Classification Search
CPC ....... A61B 8/0891; A61B 8/14; A61B 8/4209; A61B 8/4245; A61B 8/466; A61B 8/467; A61B 8/54; A61B 2562/0247; A61B 8/483; A61B 8/4254; G06T 7/10; G06T 7/62;
(Continued)

(56) References Cited

U.S. PATENT DOCUMENTS 6,574,499 B1    6/2003   Dines et al.
7,736,054 B2    6/2010   Zhang
(Continued)

FOREIGN PATENT DOCUMENTS

CN     201510300 U    6/2010
CN     103985123 A    8/2014
(Continued)

OTHER PUBLICATIONS

International Search Report and Written Opinion issued in corresponding International Application No. PCT/US2021/017204, dated Apr. 30, 2021, 12 pages.

*Primary Examiner* — Serkan Akar
*Assistant Examiner* — Neshat Baset
(74) *Attorney, Agent, or Firm* — Snyder, Clark, Lesch & Chung, LLP

(57) ABSTRACT

A track-based scanning system uses an ultrasound probe that is mechanically guided through incremental scans over an area of interest. The scanning system can be configured for different patient applications using interchangeable track stands. Two-dimensional scan data and probe position information are fed back to a base unit for processing and assembly of a three-dimensional (3D) shape model. 3D abdominal aorta segmentation and other type of analysis may be performed based on a 3D vascular shape model and an intensity model.

20 Claims, 15 Drawing Sheets

(51) Int. Cl.
*A61B 8/14* (2006.01)
*G06T 7/10* (2017.01)
*G06T 7/62* (2017.01)

(52) U.S. Cl.
CPC ............... *A61B 2562/0247* (2013.01); *G06T 2207/10136* (2013.01); *G06T 2207/30101* (2013.01); *G06T 2207/30172* (2013.01)

(58) Field of Classification Search
CPC . G06T 2207/10136; G06T 2207/30101; G06T 2207/30172
See application file for complete search history.

(56) References Cited

U.S. PATENT DOCUMENTS

| | | | |
|---|---|---|---|
| 8,139,836 B2 | 3/2012 | Arnold et al. | |
| 8,494,243 B2 | 7/2013 | Sundar et al. | |
| 8,764,666 B2 | 7/2014 | Chen | |
| 8,974,392 B2 | 3/2015 | Fujii et al. | |
| 9,414,798 B2 | 8/2016 | Feuerlein et al. | |
| 2007/0103464 A1* | 5/2007 | Kaufman | G06T 7/64 345/424 |
| 2010/0240996 A1* | 9/2010 | Ionasec | G06T 7/262 600/443 |
| 2011/0126629 A1* | 6/2011 | Nakamura | A61B 8/4281 73/644 |
| 2011/0206257 A1 | 8/2011 | Qanadli et al. | |
| 2013/0231564 A1* | 9/2013 | Zagorchev | G06T 7/62 600/447 |
| 2015/0250445 A1 | 9/2015 | Spiegel | |
| 2015/0359520 A1 | 12/2015 | Shan et al. | |
| 2019/0087957 A1 | 3/2019 | Burris | |
| 2019/0231317 A1* | 8/2019 | Anthony | A61B 8/429 |
| 2019/0261959 A1* | 8/2019 | Frankel | A61B 8/4218 |
| 2021/0183070 A1* | 6/2021 | Laaksonen | A61N 5/1048 |

FOREIGN PATENT DOCUMENTS

| | | | |
|---|---|---|---|
| CN | 204181645 U | 3/2015 | |
| CN | 104665931 A | 6/2015 | |
| CN | 106798572 A | 6/2017 | |
| CN | 108670296 A | 10/2018 | |
| DE | 3719919 A1 | 1/1988 | |
| WO | 2013171671 A1 | 11/2013 | |
| WO | WO-2013171671 A1 * | 11/2013 | ........... A61B 8/0825 |
| WO | 2018035310 A1 | 2/2018 | |

* cited by examiner

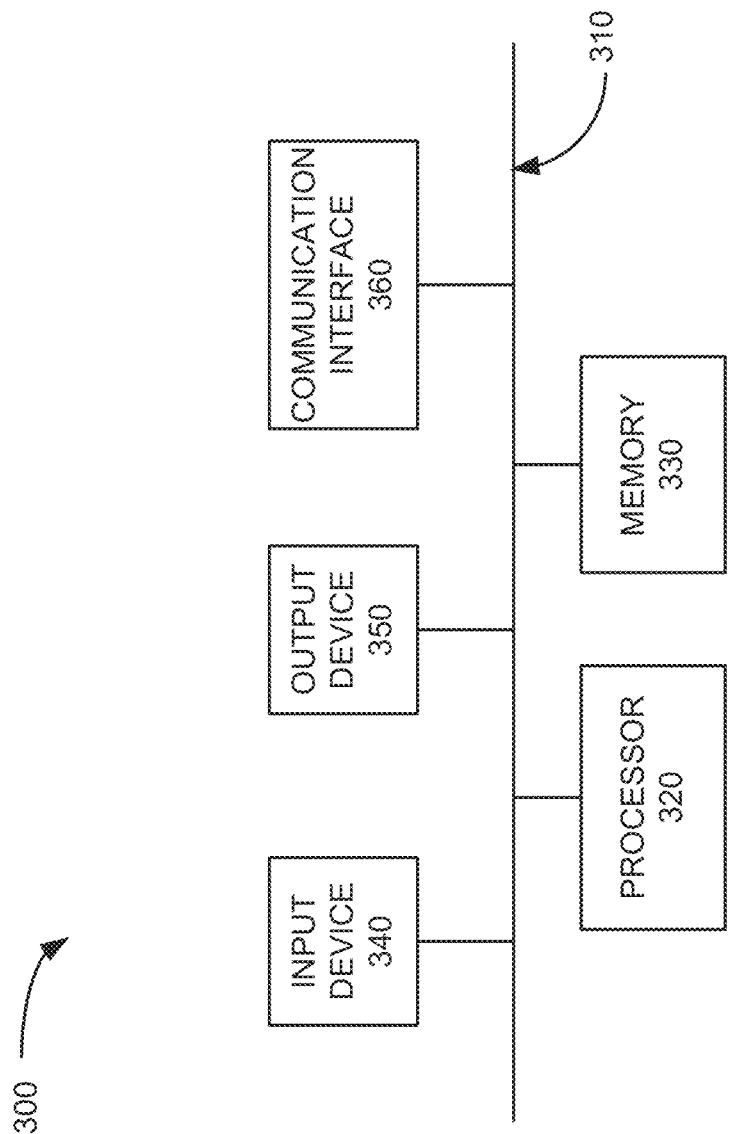

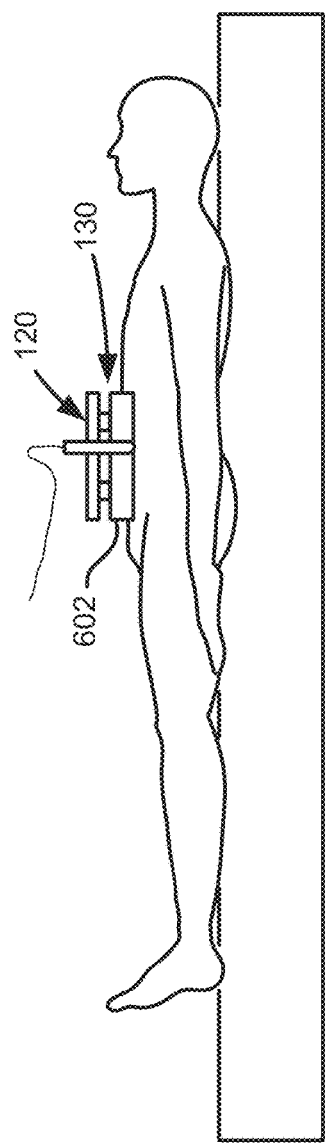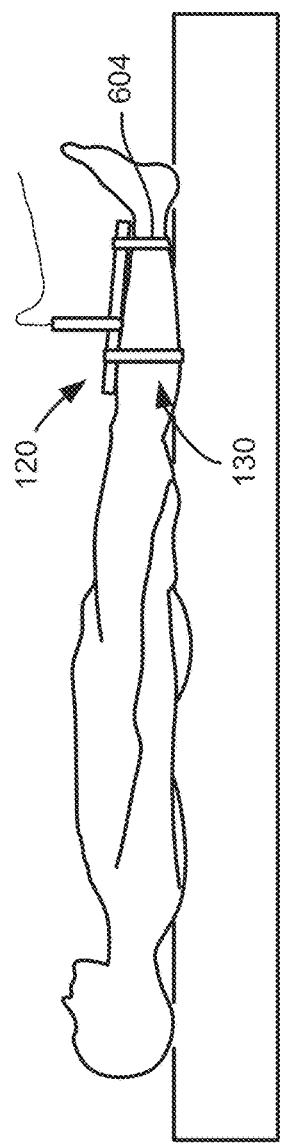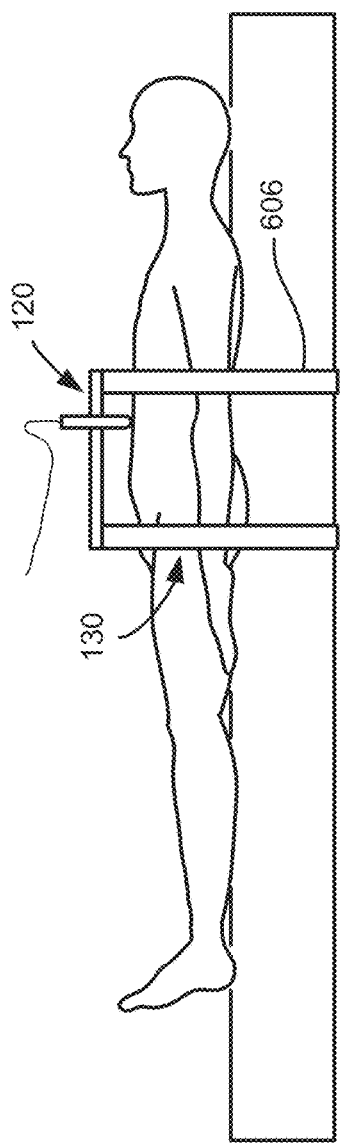

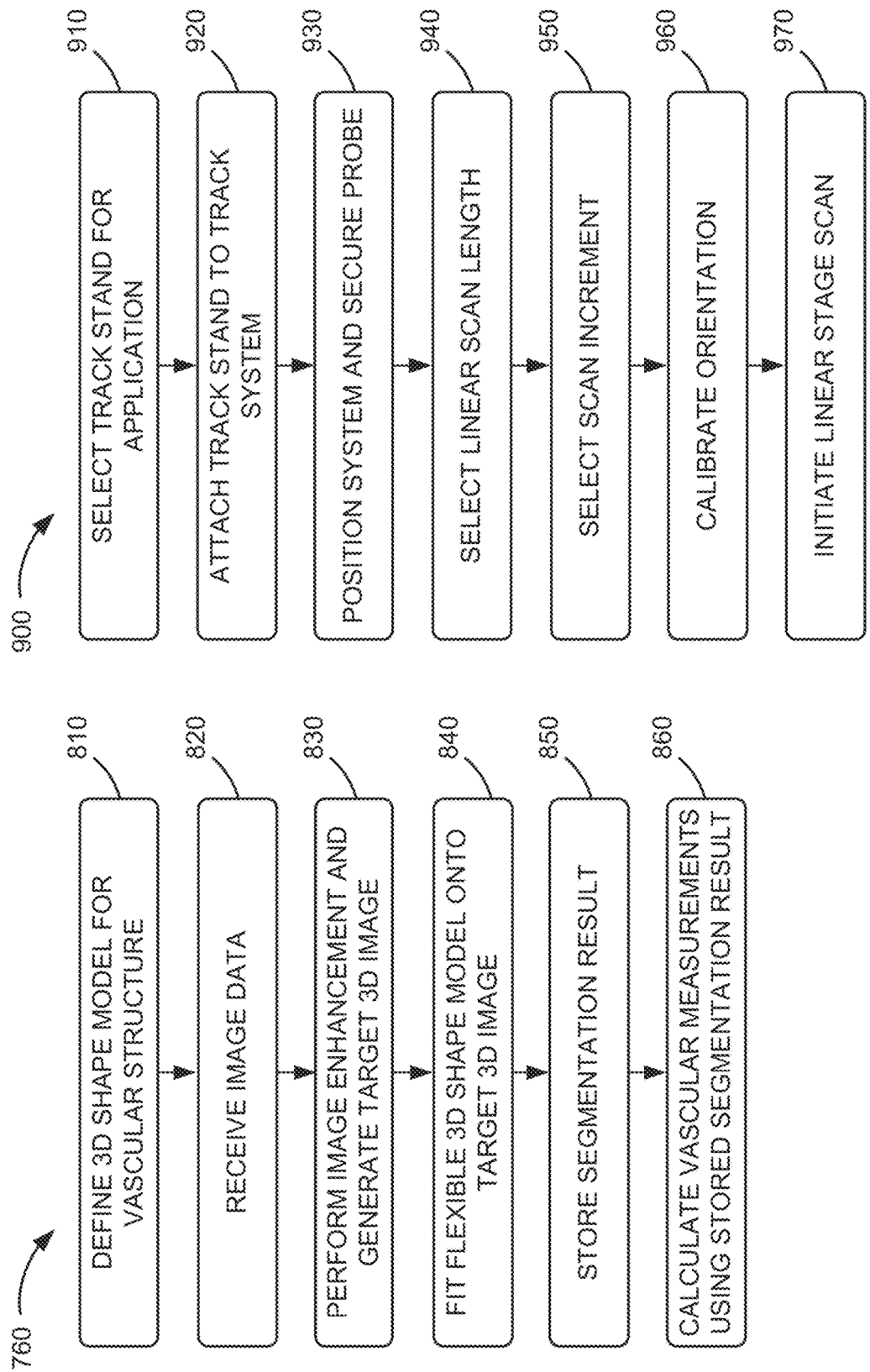

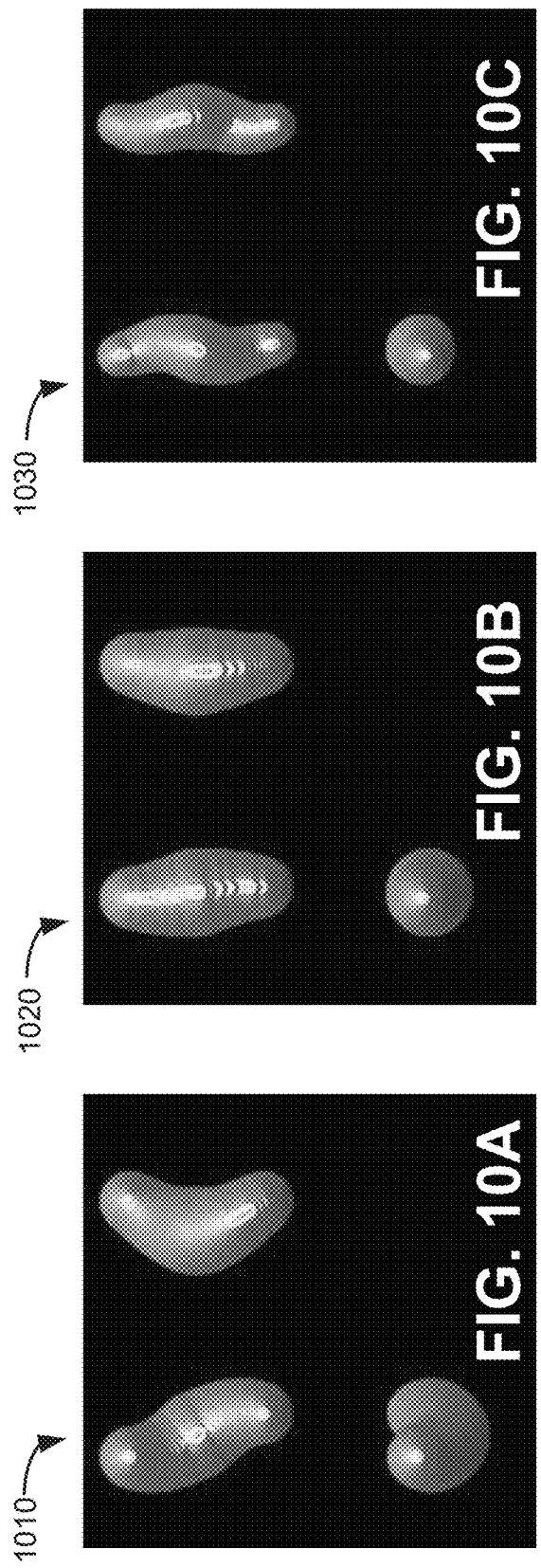
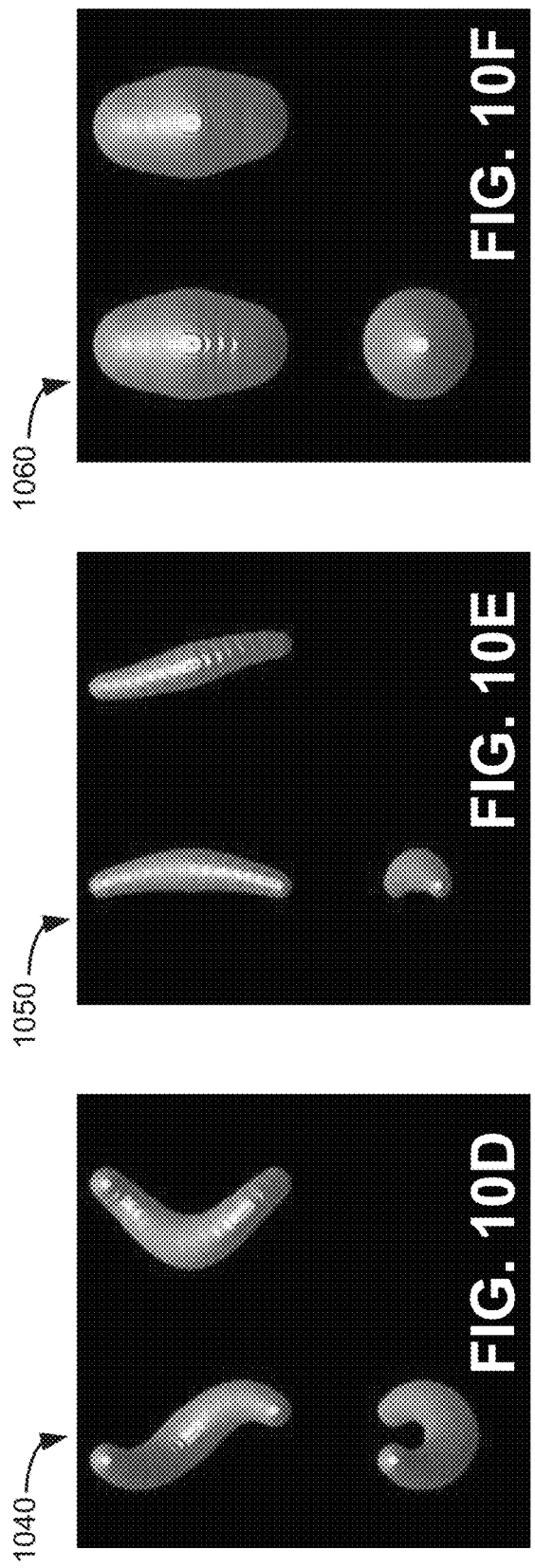

SYSTEMS AND METHODS FOR 3D ULTRASOUND IMAGING OF EXTENDED TARGETS USING INTERCHANGEABLE TRACK STANDS

CROSS-REFERENCE TO RELATED APPLICATION

This application claims priority under 35 U.S.C. § 119, based on U.S. Provisional Patent Application No. 62/980,514 filed Feb. 24, 2020, titled "System and Methods for 3D Ultrasound Imaging of Extended Organs," the disclosure of which is hereby incorporated by reference.

BACKGROUND INFORMATION

Abdominal aortic aneurysm (AAA) refers to a dilatation of the aorta between the diaphragm and the aortic bifurcation and, by convention, can be defined as an abdominal aortic diameter of thirty (30) millimeters (mm) or more in either anterior-posterior or transverse planes. Ultrasound imaging is a common modality for screening patients suffering from AAA. Although ultrasound imaging provides inexpensive and non-invasive real-time imaging, the image quality is lower compared with other imaging modalities, such as computed tomography (CT). Furthermore, the image quality of ultrasound imaging typically becomes more degraded when scanning long organs or vascular structures, such as the abdominal aorta.

BRIEF DESCRIPTION OF THE DRAWINGS

FIG. 3 illustrates an exemplary configuration of components included in one or more of the elements of FIG. 1, FIG. 2A, or FIG. 2B;

FIGS. 6A-6C are illustrations of exemplary track stand configurations, according to implementations described herein;

FIG. 8 is a flow diagram illustrating an exemplary process for identifying parameters or elements associated with a target of interest;

FIG. 9 is a flow diagram illustrating an exemplary process for a user to employ the scanning system of FIG. 1 to perform an ultrasound scan;

FIGS. 10A-10F illustrate simulated aorta data sets that can be used for a 3D shape model in accordance with the process of FIG. 8;

DETAILED DESCRIPTION OF PREFERRED EMBODIMENTS

Figure 1:
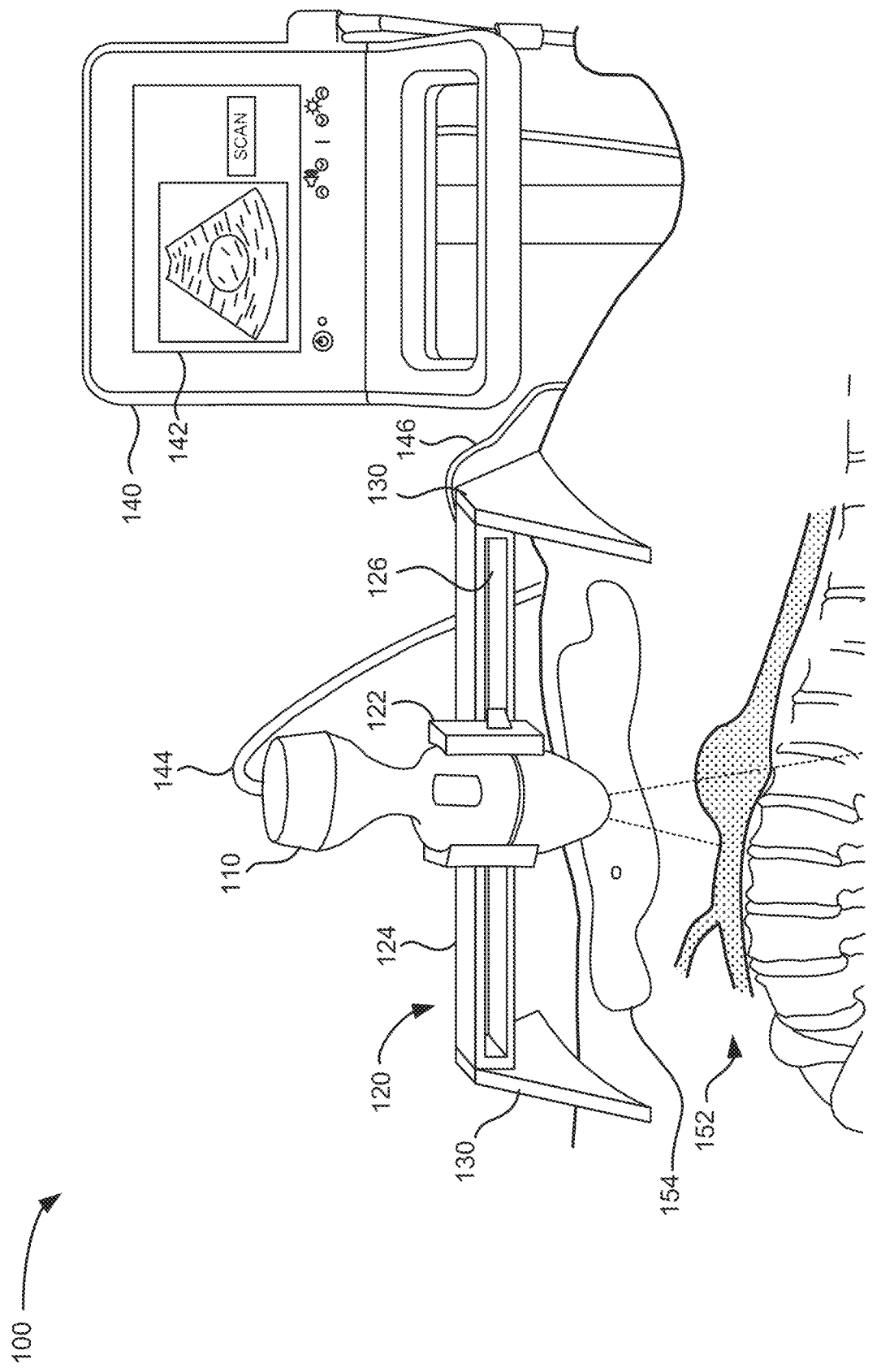
FIG. 1 is a schematic of a scanning system in which systems and methods described herein may be implemented.

The following detailed description refers to the accompanying drawings. The same reference numbers in different drawings may identify the same or similar elements. Also, the following detailed description does not limit the invention.

A conventional way to use ultrasound system is to move an ultrasound probe over the subject's body surface to image a region of interest (ROI). The probe will collect reflected ultrasound signals (or echoes) to generate a two-dimensional (2D) B-mode ultrasound image. The 2D ultrasound image includes a cross-sectional view of the ROI. An experienced operator may collect images to form a mentally constructed volume of the ROI for examination of the organ features and estimation of the volume of the target. This approach can be time consuming and may provide an inaccurate reconstructed image. Also, using conventional methods, coronal and longitudinal information are difficult to visualize and analyze.

Three-dimensional (3D) ultrasound imaging can enhance the understanding of a scanned ROI. 3D ultrasound scans generally include multiple 2D ultrasound images and their relative spatial information. Currently, 3D ultrasound can be achieved using various technologies, including use of (a) a matrix transducer, (b) a standard curved transducer adapted for freehand scanning using optical tracking, (c) a standard linear transducer adapted for freehand scanning using magnetic tracking, or (d) a mechanical transducer. Each of these technologies includes various limitations and advantages. For example, a matrix transducer is fast and accurate; but is also expensive, has limited coverage, and is not easily interchangeable between different ultrasound systems. Conversely, freehand scanning (with either optical or magnetic tracking) has lower-costs with more scanning flexibility, but generates less accurate reconstructed 3D images.

Mechanical transducers offer improved imaging over freehand systems by moving a transducer in a predefined translation and orientation path over a ROI. Mechanical transducers are able to acquire regularly spaced 2D ultrasound images with accurate position and orientation that is relative to a frame. Thus, mechanical transducers can be used to generate an accurate 3D ultrasound reconstruction image with lower costs than, for example, a matrix transducer. However, mechanical transducers are limited in their applications and do not easily adapt to different or irregular (e.g., human) shapes. Furthermore, mechanical transducers cannot capture completely accurate images for large and long structures, such as a human abdominal aorta.

The accuracy or usefulness of ultrasound images may be improved by segmentation and qualitative analysis. For example, effective data interpretation of reconstructed 3D images can help compensate for less precise imagery. Manual or semi-automated methods have been used to segment the abdominal aorta from an ultrasound image, which needs special knowledge and consistency. Automated segmentation approaches are based on individual 2D image slices, such as 2D active contour or graphic searching, which lack consistency and also are vulnerable to noise and artifacts in 3D space.

Thus, there remains a need for a 3D ultrasound imaging solution that is low-cost, accurate, multifunctional, and can cover a large ROI. The 3D ultrasound imaging solution may balance low-cost image collection techniques with segmentation and quantitative analysis methods that maximize the value of the scan data.

Implementations described herein provide a track-based scanning system using a conventional 2D probe that is mechanically guided through incremental scans over an area of interest. The scanning system can be configured for different patient applications using interchangeable track stands. The 2D scan data and probe position information are fed back to a base unit for processing and assembly of a 3D shape model. Organ analysis, such as 3D abdominal aorta segmentation, for example, may be performed based on a 3D shape model and an intensity model.

For example, in some implementations, a flexible 3D aorta model is applied to 3D echo data to provide image segmentation for structures of interest, such as the abdominal aorta (or other blood vessels) or other structures of interest (e.g., an aneurysm) based on information obtained via an ultrasound scanner. The flexible 3D aorta model is defined based on the human abdominal aorta, with possible variations integrated into the shape model. Fitting the flexible 3D aorta model to a new echo data set can be defined as minimizing a special energy function. In some implementations, the flexible 3D aorta model may be a defined segment. In other implementations, the flexible 3D aorta model may be open-ended (e.g., without length restrictions). The intensity model can also be defined by analyzing the ultrasound image brightness inside and outside the aorta structures. Segmentation is the first step for quantitative analysis in AAA evaluation using 3D ultrasound imaging. With abdominal aorta segmentation complete, post processing steps, such as centerline extraction and maximum diameter calculations, can be easily determined.

FIG. 1 is a schematic of a scanning system 100 in which systems and methods described herein may be implemented. Referring to FIG. 1, scanning system 100 includes a probe 110 operating on a track structure 120, a track stand 130, a base unit 140, and a cable 144.

Probe 110 includes a handle portion, a trigger, and a nose (or dome) portion. One or more ultrasound transceivers, located in the nose portion, may be activated to transmit ultrasound signals toward a target object of interest, which may include an organ (e.g., a bladder, an aorta, a kidney, etc.) or a non-organ structure (e.g., a catheter, a needle, or another medical device). For example, as shown in FIG. 1, probe 110 is located on an abdominal area of patient 150 and over an extended target of interest 152, which in this example is the abdominal aorta. The dome of probe 110 is typically formed of a material that provides an appropriate acoustical impedance match to an anatomical portion and/or permits ultrasound energy to be properly focused as it is projected into the anatomical portion. For example, an acoustic gel or gel pads, illustrated at area 154 in FIG. 1, may be applied to patient's skin over the region of interest to provide an acoustical impedance match when the dome is placed against the skin.

Probe 110 includes one or more ultrasound transceiver elements and one or more transducer elements within the dome that transmit ultrasound energy outwardly from the dome, and receive acoustic reflections or echoes generated by internal structures/tissue within the anatomical portion. For example, the one or more ultrasound transducer elements may include a one-dimensional, or a two-dimensional array of piezoelectric elements that may be moved within the dome by a motor to provide different scan directions with respect to the transmission of ultrasound signals by the transceiver elements. Alternatively, the transducer elements may be stationary with respect to probe 110 so that the selected anatomical region may be scanned by selectively energizing the elements in the array. According to implementations described herein, probe 110 may be equipped with an imaging application (or "app") that may be used to interface with base unit 140. Base unit 140 may, for example, communicate via the imaging application to actuate ultrasound signal transmissions from probe 110.

According to implementations described herein, probe 110 may be secured to a mechanical track structure 120. As described further herein, track structure 120 may include a probe holder 122 and a track frame 124 that forms a track 126. Probe holder 122 may secure probe 110 in track structure 120 and advance probe 110 along a linear path of a track 126 in track frame 124. Probe holder 122 may slide or move along track 126. According to an implementation, a linear stage actuator and a step motor (not shown in FIG. 1) may be used to control the scanning location of probe 110 and image collection along the linear path of track 126. According to another implementation, probe 110 may be manually moved along track 126 in an indexed manner, with the location of probe 110 being detected by base unit 140. Track structure 120 may be fitted to an application-based track stand 130. For example, track stand 130 may be one of multiple track stands specially designed for a particular scanning application (e.g., abdominal, leg, arm, etc.). As described further herein, different track stands 130 may be interchangeable with track structure 120 for use in different applications.

Base unit 140 may control operation of probe 110 and track structure 120. Base unit 140 may communicate with probe 110 via a wired connection, such as via cable 144, and track structure 120 via a different wired connection, such as cable 146. In other implementations, probe 110 and track structure 120 may communicate with base unit 140 via a wireless connection (e.g., Bluetooth, Wi-Fi, etc.). Generally, base unit 140 may control and/or detect the location and actuation of probe 110 to collect a sequence of 2D ultrasound images. In one implementation, base unit 140 can control movement of probe holder 122 in a predefined translation and orientation path over an extended target (e.g., an organ or a non-organ structure with a length that exceeds the scan coverage of probe 110), such as extended target 152. Base unit 140 can acquire regularly spaced 2D ultrasound frames that can be collected and integrated into a 3D ultrasound volume via a reconstruction process. In another implementation, base unit 140 may detect movement (e.g., manually indexed movement, geared movement, etc.) of probe holder 122 along track 126 and acquire regularly spaced 2D ultrasound frames.

Base unit 140 includes a display 142 to allow an operator to view processed results from an ultrasound scan, and/or to allow operational interaction with respect to the operator during operation of probe 110. For example, display 142 may include an output display/screen, such as a liquid crystal display (LCD), light emitting diode (LED) based display, or other type of display that provides text and/or image data to an operator. For example, display 142 may provide artifact visualizations overlaid on B-mode images to help determine the quality/accuracy of an ultrasound scan. Display 142 may also display two-dimensional or three-dimensional images of the selected anatomical region.

To scan a selected anatomical portion of a patient, the dome of probe 110 may be positioned against a surface portion of patient 150 as illustrated in FIG. 1 that is proximate to the anatomical portion to be scanned. The operator installs probe 110 in the probe holder 122 and performs a calibration process. Base unit 140 may cause track structure 120 to move probe 110 along track 126 and actuate the transceiver and transducer elements at known intervals, causing the transceiver to transmit ultrasound signals into the body and receive corresponding return echo signals that may be at least partially processed by the transceiver to generate an ultrasound image of the selected anatomical portion. In a particular embodiment, the transceiver transmits ultrasound signals with the center frequency in a range that extends from approximately about two megahertz (MHz) to approximately 10 MHz or more.

Figure 2A:
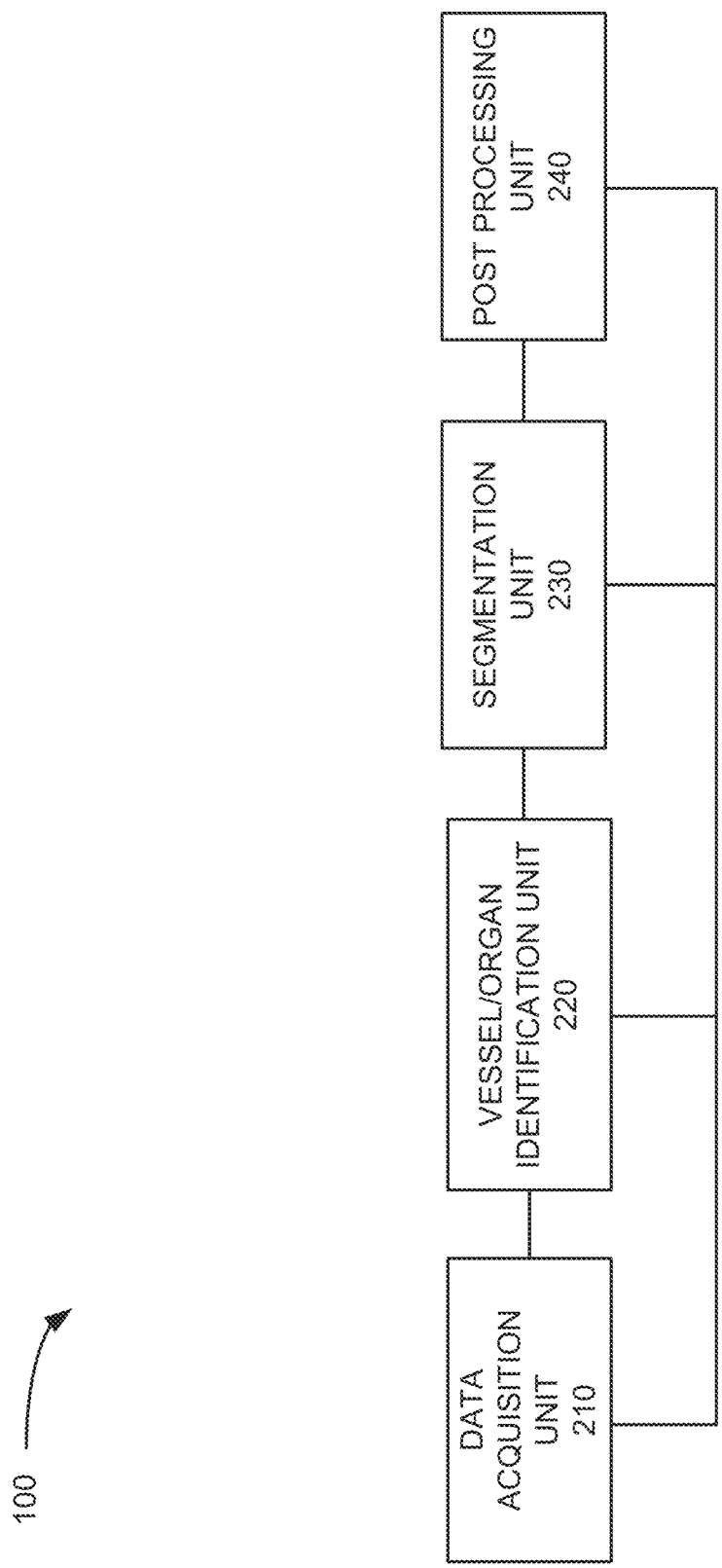
FIGS. 2A and 2B illustrate an exemplary configuration of logic elements included in the scanning system of FIG. 1.
Figure 2B:
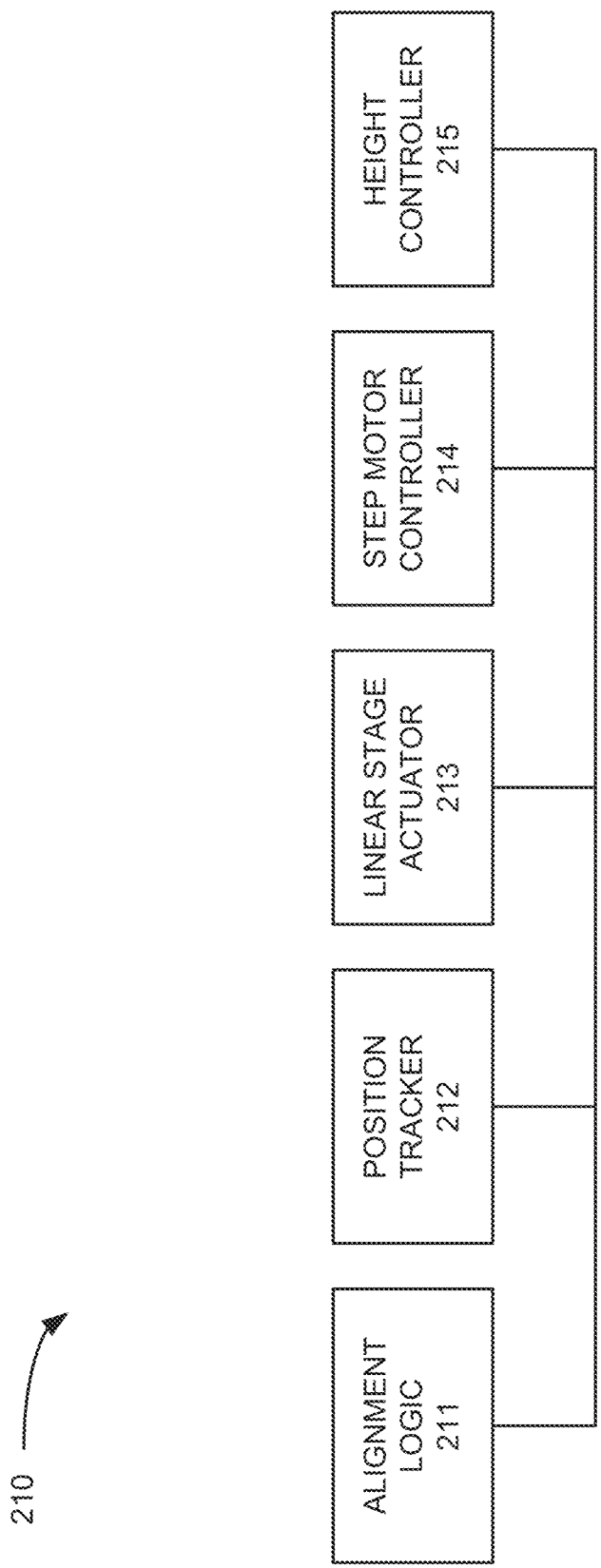

FIGS. 2A and 2B are block diagrams of functional logic components implemented in scanning system 100 in accordance with an exemplary implementation. Referring to FIG. 2A, system 100 includes a data acquisition unit 210, a vessel/organ identification unit 220, a segmentation unit 230, and post-processing unit 240. In an exemplary implementation, data acquisition unit 210 may be distributed between probe 110 and base unit 140 and the other functional units (e.g., vessel/organ identification unit 220, segmentation unit 230, and post-processing unit 240) and may be implemented in base unit 140 and/or probe 110. In other implementations, the particular units and/or logic may be implemented by other devices, such as via computing devices or servers located externally with respect to both probe 110 and base unit 140 (e.g., accessible via a wireless connection to the Internet or to a local area network within a hospital, etc.). For example, probe 110 may transmit echo data and/or image data to a processing system via, for example, a wireless connection (e.g., Wi-Fi or some other wireless protocol/technology) that is located remotely from probe 110 and base unit 140.

As described above, probe 110 may include one or more transceivers that produces ultrasound signals, receives echoes from the transmitted signals and generates B-mode image data based on the received echoes. In an exemplary implementation, data acquisition unit 210 uses probe 110 and track structure 120 to obtain data associated with multiple scan planes corresponding to the region of interest in a patient. For example, probe 110 may receive echo data, collected along various known locations along track 126, that is processed by data acquisition unit 210 to generate 2D B-mode image data to determine a size of a vessel (such as the abdominal aorta and/or the size of an aneurysm in the abdominal aorta). In other implementations, probe 110 may receive echo data that is processed to generate 3D image data that can be used to determine the size of the vessel. Data acquisition unit 210 is described further in connection with FIG. 2B.

As shown in FIG. 2B, data acquisition unit 210 may include alignment logic 211, a position tracker 212, a linear stage actuator 213, a step motor controller 214, and a height controller 215. In one implementation, components of alignment logic 211, position tracker 212, linear stage actuator 213, step motor controller 214, and height controller 215 may be included in a software package or application to integrate scanning system 100 with base unit 140.

Alignment logic 211 may include instructions to confirm probe 110 is properly oriented and positioned in probe holder 122. According to an implementation, alignment logic 211 may communicate with probe 110 to obtain gyroscopic data and/or accelerometer data to confirm, for example, that probe 110 is secured in probe holder 122 with a predominantly vertical orientation with respect to track frame 124.

Position tracker 212 may include instructions to receive and record position information of probe holder 122, such as the linear position of probe holder 122 relative to track 126. In other embodiments described further herein, position tracker 212 may also receive and record vertical (e.g., height) position information relative to, for example, track frame 124. Position tracker 212 may associate position information with echo data collected by probe 110 when the probe is in a particular position.

Linear stage actuator 213 may include instructions to actuate probe 110 when probe holder 122 positions probe 110 at different incremental positions along, for example, track 126. Linear stage actuator 213 may, for example, use application programming interface (API) calls that are communicated through cable 144 (or wirelessly) to probe 110 to initiate transmission of ultrasound signals and collection of corresponding echo data.

Step motor controller 214 may include instructions to control movement of probe holder 122 along track 126. For example, step motor controller 214 may cause a motor (not shown in FIG. 1) to incrementally move probe holder 122 into different scanning locations along track 126.

Height controller 215 may include instructions to control vertical movement of probe holder 122. As described further herein, height controller 215 may detect pressure readings from a pressure sensor on scanning system 100 (not shown in FIG. 1) and adjust the relative height of probe holder 122 to either ensure contact of the probe 110 nose with the patient or to ensure excessive force is not applied to the patient.

Returning to FIG. 2A, vessel/organ identification unit 220 may perform pre-processing of an image and detect if a vessel or organ is present within a region of interest based on, for example, differentiation of pixel intensity (e.g., as scanned and collected by data acquisition unit 210). As examples of pre-processing, vessel/organ identification unit 220 may apply noise reduction, adjust the aspect ratio of the raw B-mode image, and/or apply a scan conversion. As an example of vessel identification, in a 2D image, a blood carrying vessel may be identified as a dark region within an area of lighter-shaded pixels, where the lighter-shaded pixels typically represent body tissues. In another implementation, vessel/organ identification unit 220 may include artifact detection logic to detect particular structures adjacent the aorta, similar to that used in bladder scanning.

Segmentation unit 230 may receive data from data acquisition unit 210 and/or vessel/organ identification unit 220 and apply image processing using a 3D vascular shape model to segment, for example, the abdominal aorta. The 3D vascular shape model may include simulated 3D AAA shapes derived from human samples. An intensity model may include ultrasound image brightness information derived from human samples. In one implementation, segmentation unit 230 may apply a flexible 3D vascular shape model to a target 3D image. For example, as described in more detail below, segmentation unit 230 may fit a 3D vascular shape to a target image data set by minimizing one of several possible energy functions.

Post processing unit 240 includes logic to identify a size of an abdominal aorta that includes an aneurysm located in the abdominal aorta, as well as identify the size (e.g., diameter) and centerline of the aneurysm. For example, post processing unit 240 can provide a 3D reconstruction function to fully construct the aorta structure by combining all segmentation results associated with received echo data. In this manner, the measurement of the aorta diameter will be more accurate as compared to using conventional 2D imaging, as described in detail below.

The exemplary configuration illustrated in FIGS. 2A and 2B is provided for simplicity. Scanning system 100 may include more or fewer logic units/devices than illustrated in FIGS. 2A and 2B. For example, system 100 may include multiple data acquisition units 210 and multiple processing units that process the received data. In addition, system 100 may include additional elements, such as communication interfaces (e.g., radio frequency transceivers) that transmit and receive information via external networks to aid in analyzing ultrasound signals to identify a target in a region of interest. Furthermore, while illustrations and descriptions herein primarily refer to blood vessel applications (e.g., identifying an abdominal aorta and/or an aneurism within the abdominal aorta), other embodiments may be applied to other vascular structures and organs, such as the bladder, prostate/kidney boundary, thyroid, etc.

FIG. 3 illustrates an exemplary configuration of a device 300. Device 300 may correspond to, for example, a component of data acquisition unit 210, vessel/organ identification unit 220, segmentation unit 230, and/or post processing unit 240. Device 300 may also correspond to elements in FIG. 1, such as probe 110 and/or base unit 140. Referring to FIG. 3, device 300 may include bus 310, processor 320, memory 330, input device 340, output device 350 and communication interface 360. Bus 310 may include a path that permits communication among the elements of device 300.

Processor 320 may include one or more processors, microprocessors, or processing logic that may interpret and execute instructions. Memory 330 may include a random access memory (RAM) or another type of dynamic storage device that may store information and instructions for execution by processor 320. Memory 330 may also include a read only memory (ROM) device or another type of static storage device that may store static information and instructions for use by processor 320. Memory 330 may further include a solid state drive (SSD). Memory 330 may also include a magnetic and/or optical recording medium (e.g., a hard disk) and its corresponding drive.

Input device 340 may include a mechanism that permits a user (e.g., a technician) to input information to device 300, such as a keyboard, a keypad, a mouse, a pen, a microphone, a touch screen, voice recognition and/or biometric mechanisms, etc. Output device 350 may include a mechanism that outputs information to the technician, including a display (e.g., a liquid crystal display (LCD)), a printer, a speaker, etc. In some implementations, a touch screen display may act as both an input device and an output device.

Communication interface 360 may include one or more transceivers that device 300 uses to communicate with other devices via wired, wireless or optical mechanisms. For example, communication interface 360 may include one or more radio frequency (RF) transmitters, receivers and/or transceivers and one or more antennas for transmitting and receiving RF data via a network. Communication interface 360 may also include a modem or an Ethernet interface to a LAN or other mechanisms for communicating with elements in a network.

The exemplary configuration illustrated in FIG. 3 is provided for simplicity. It should be understood that device 300 may include more or fewer devices than illustrated in FIG. 3. In an exemplary implementation, device 300 performs operations in response to processor 320 executing sequences of instructions contained in a computer-readable medium, such as memory 330. A computer-readable medium may be defined as a physical or logical memory device. The software instructions may be read into memory 330 from another computer-readable medium (e.g., a hard disk drive (HDD), SSD, etc.), or from another device via communication interface 360. Alternatively, hard-wired circuitry, such as application specific integrated circuits (ASICs), field programmable gate arrays (FPGAs), etc., may be used in place of or in combination with software instructions to implement processes consistent with the implementations described herein. Thus, implementations described herein are not limited to any specific combination of hardware circuitry and software.

Figure 4A:
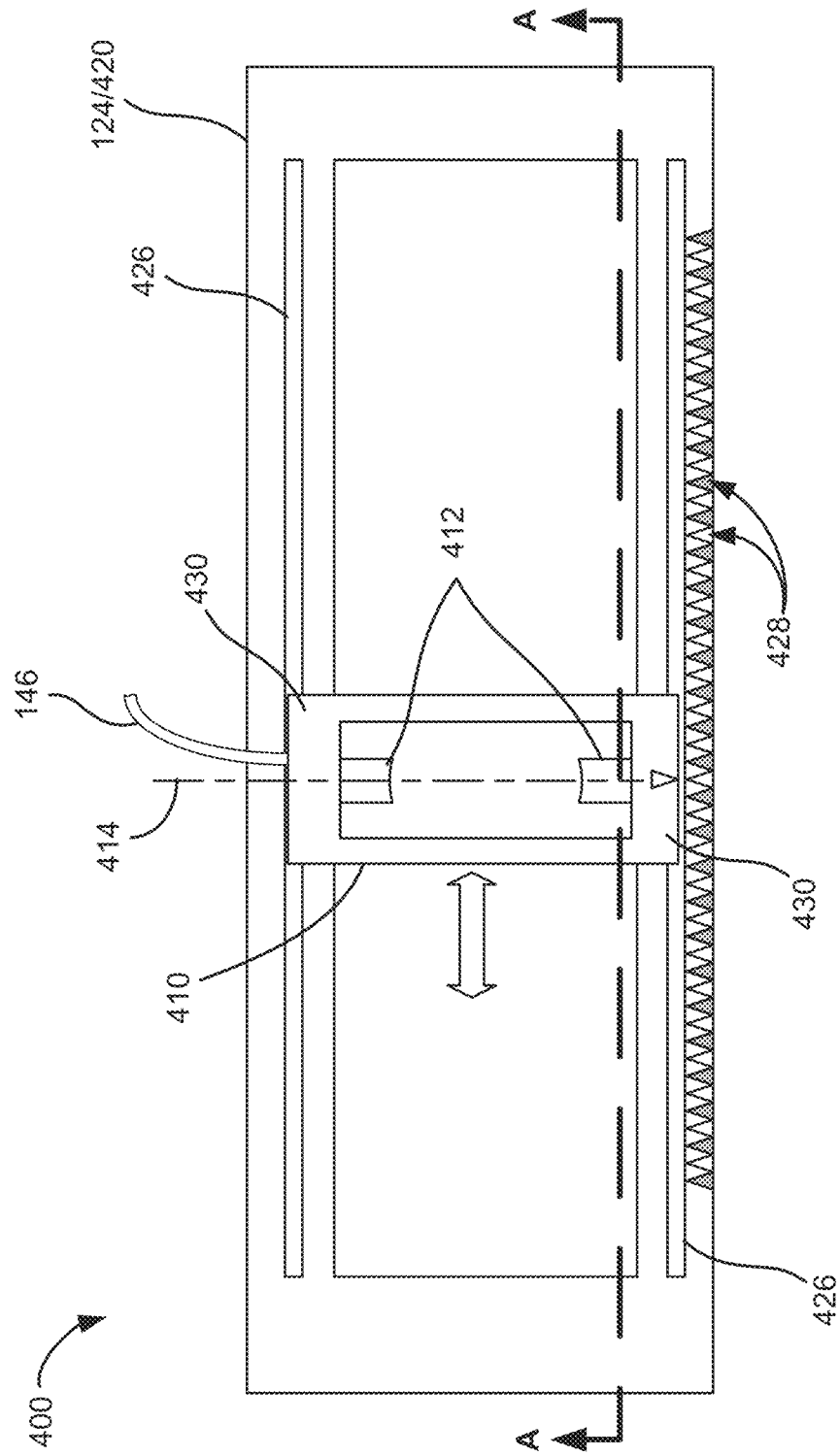
FIGS. 4A-4C are respective top, end, and cross-sectional views of a portion of the track structure of FIG. 1, according to an implementation.
Figure 4B:
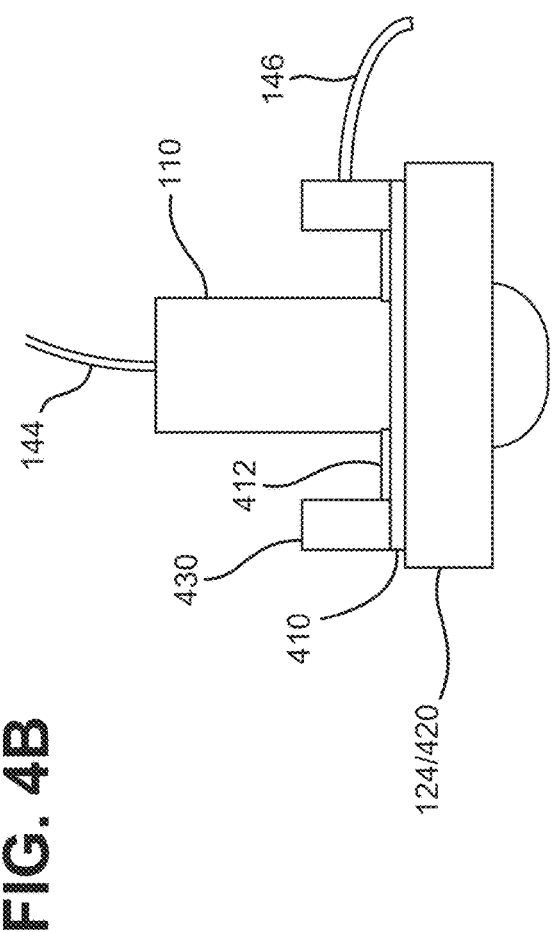
Figure 4C:
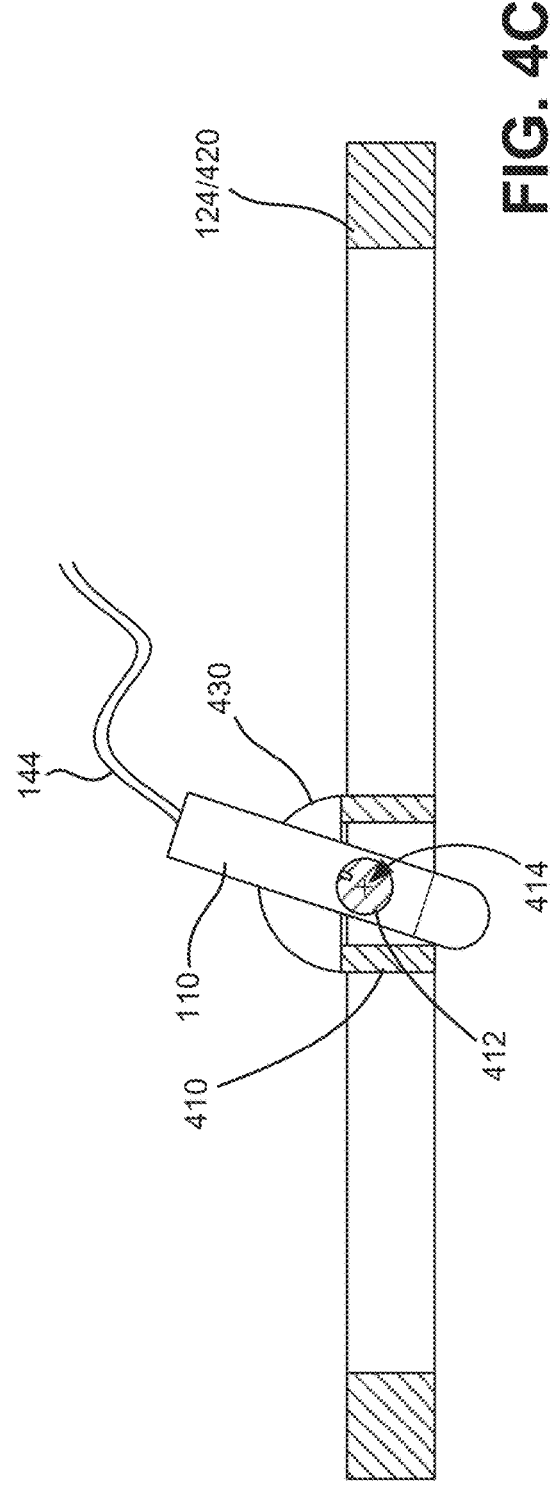

FIG. 4A is a schematic top view of dual track system 400 that may correspond to track structure 120 according to an implementation. FIG. 4B is an end view of dual track system 400 with probe 110 installed. FIG. 4C is a side cross-section view along A-A of FIG. 4A, shown with probe 110 installed. Referring collectively to FIGS. 4A-4C, dual track system 400 may include a moving block 410 mounted to a track frame 420. Moving block 410 may include rotational probe holders 412, which together may correspond to probe holder 122. Frame 420 may correspond to track frame 124.

Frame 420 may be mounted on or over a region of interest on a patient. One or more step motors 430 in, for example, block 410 may incrementally advance block 410 along tracks 426. Increment markers 428 may be tracked to accurately determine a relative linear position of moving block 410. For example, according to an implementation, increment markers 428 may be individually identifiable and selected to mark starting and ending points for a linear scan.

A shown in FIGS. 4B and 4C, probe 110 may be secured between rotational probe holders 412. For example, rotational probe holders 412 may grip or pinch probe 110 to maintain probe 110 in a consistent linear position relative to moving block 410. Rotational probe holders 412 may allow probe 110 to be installed at different rotational orientations (e.g., relative to an axis of rotation 414). According to an implementation, rotational probe holders 412 may include a locking mechanism to hold probe 110 at a known angle that may be determined by a reference gyroscope in probe 110 prior to initiating a scan.

According to one embodiment, cable 146 may be used to provide communications between dual track system 400 and base unit 140, while another cable 144 may provide communications between probe 110 and base unit 140. Thus, base unit 140 may control/monitor the scanning location of probe 110 and image collection along the linear path of tracks 426.

Figure 5:
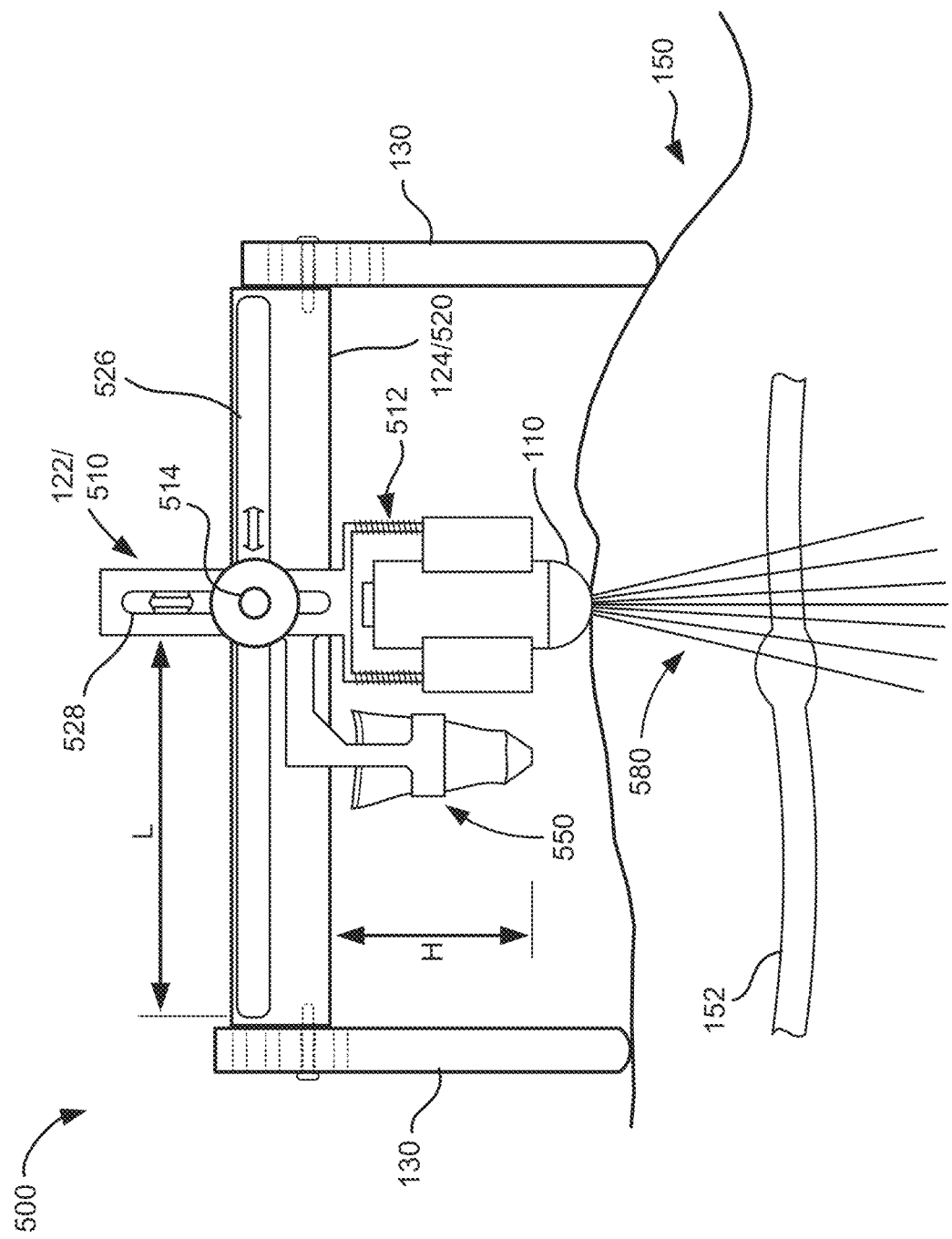
FIG. 5 illustrates a side view of a portion of the scanning system of FIG. 1, in accordance with another exemplary implementation.

FIG. 5 is a schematic side view of single track system 500 that may correspond to scanning system 100 according to an implementation. Single track system 500 may include an adjustable height probe holder 510 mounted to a track frame 520. Probe holder 510 may correspond to probe holder 122 and may position probe 110 to direct scans 580 (e.g., ultrasound signals) toward patient 150. Frame 520 may correspond to track frame 124. In FIG. 5, track frame 520 is shown attached to track stand 130 and mounted on the torso of a patient 150. Frame 520 may include a linear track 526 that is generally positioned parallel (e.g., horizontal) to an extended target 152 (e.g., an abdominal aorta) on patient 150. Probe holder 510 may include a linear track 528 that is oriented perpendicular to linear track 526.

To accommodate scanning of a non-flat surface, such as a patient's abdomen, probe holder 510 may adjust and monitor a height (H) of probe holder 510 relative to frame 520, along with the linear position (L) within track frame 520. The height and linear position may be collectively referred to as location information. The location information may be used when constructing the 3D volumetric image data from 2D ultrasound scans.

According to an implementation, probe holder 510 may include one or more pressure sensors 512 and height adjustors 514. Pressure sensors 512 may indirectly measure the pressure/force applied between a patient and the nose of probe 110. Height adjustor 514 may include a motor or mechanical system to move probe holder 510 up or down relative to track frame 520. As probe holder 510 moves incrementally along track 526, control logic (e.g., height controller 215) in base unit 140 may signal height adjustor 514 to adjust the height of probe holder 510 to maintain consistent pressure readings (e.g., within a threshold window) from pressure sensor 512 at each scanning location along track 526. The location information of probe holder 510 may be recorded and associated with each incremental scan 580 performed along track 526. Thus, base unit 140 may account for both the linear position and height position of probe 110 (or probe holder 122) at each increment.

According to another implementation, track system 500 may include an integrated gel dispenser 550. Gel dispenser 550 may be attached to a portion of probe holder 510. Gel dispenser 550 may be configured to automatically eject gel (e.g., acoustic gel 154 of FIG. 1) onto a patient at a location close to the tip of probe 110. Thus, gel dispenser 550 may provide sufficient gel to allow for acoustic coupling and lubrication while scanning is in progress. According to an implementation, gel dispenser 550 may be adjustable to lead probe 110 in either direction of a linear scan. Gel dispenser 550 may be incorporated into single track or double track configurations of track systems described herein.

Track stand 130 may include one or more components that may interchangeably connect to frame 520. In one implementation, track stand 130 may include adjustable height guides, such as slots, pins, or different interlocking positions, to allow frame 520 to be mounted at a preferred orientation (e.g., substantially parallel to the surface of patient 150). In addition to abdominal applications, track stand 130 may be configured for other applications, such as a whole-arm ultrasound for Upper-Extremity Deep Venous Thrombosis detection or a lower extremity (e.g., leg) venous system for Deep Venous Thrombosis detection.

Different types of track stands 130 may be attached to track structure 120 for different applications. FIGS. 6A-6C provide illustrations of other track stand 130 configurations according to implementations described here. FIG. 6A illustrates a track stand 130 on a human abdomen for aorta scanning, according to an embodiment. In the configuration of FIG. 6A, track stand 130 may include rails 602 that are substantially parallel to track 126. Rails 602 may rest on the patient to support track structure 120 above the patient's abdomen.

FIG. 6B illustrates a track stand 130 on a human limb (e.g., a leg), according to an embodiment. In the configuration of FIG. 6B, track stand 130 may include a pair of hoops 604 which wrap around the limb and attach to track structure 120. In one implementation, hoops 604 may include flexible materials, such as cloth bands or nylon belts that can be cinched around the patient's limb. In another implementation, hoops 604 may include a rigid or semi-rigid material that may bend around the patient's limb. The configuration of FIG. 6B may be used, for example, for Deep Venous Thrombosis detection in a patient's leg.

FIG. 6C illustrates a track stand 130 on a human torso, according to another embodiment. In the configuration of FIG. 6C, track stand 130 may include a pair of legs 606 that are attached to a table or bed that supports the patient. Legs 606 also attach to track structure 120. In one implementation, legs 606 may include height adjustors to allow the angle of track structure 120 to allow frame 124 of track structure 120 to be mounted at a preferred orientation (e.g., substantially parallel to the scanned surface of the patient).

Figure 7:
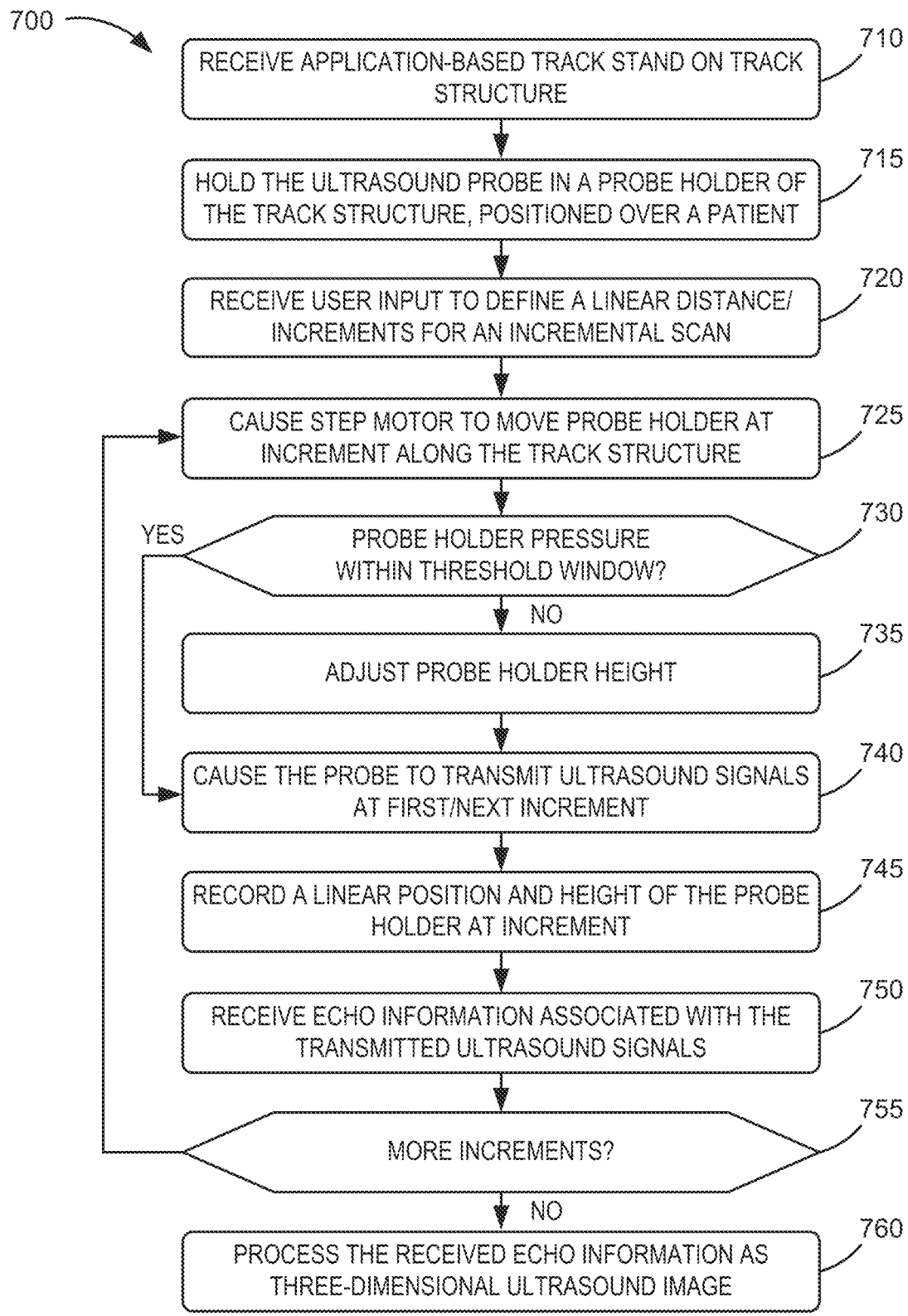
FIG. 7 is a flow diagram of an exemplary process for performing an incremental linear ultrasound scan.

FIG. 7 is a flow diagram illustrating an exemplary process 700 of performing an incremental linear ultrasound scan. Process 700 may be performed, for example, by scanning system 100. Process 700 may include receiving an application-based track stand on a track structure (block 710), and holding an ultrasound probe in a probe holder of the track structure, positioned over a patient (block 715). For example, a technician may select an appropriate track stand 130 for scanning system 100 to be used over a particular area of interest (e.g., a patient's abdomen, an arm, a leg, etc.). The technician may attach track stand 130 to the track structure 120, secure probe 110 to probe holder 122, and position scanning system 100 on/over the patient.

Process 700 may also include receiving user input to define a linear distance (e.g., in inches or centimeters) and/or increments for an incremental scan (block 720) and causing a step motor to move the probe holder at an increment along the track structure (block 725). For example, a technician may input (e.g., into base unit 140) a linear distance for movement of probe holder 122. The linear distance may include, for example, a start and a stop point along a track (e.g., particular increment markers 428 along track 426). Additionally, or alternatively, a technician may input the amount or interval of increments to be used in a scan. For example, a technician may select use of every available increment marker 428 for a most precise scan, with longer scan time, or a technician may select alternating increment markers 428 (e.g. every other increment or every third increment marker 428) to a less precise and faster scan. Based on the technician input, base unit 140 may initiate a step motor (e.g., step motor 430) to position probe holder 122 to a starting position (if necessary).

Process 700 may include determining if the probe holder pressure is within a threshold window (block 730). For example, when probe holder 122 is in the correct linear position, a pressure sensor (e.g., pressure sensor 512) may detect pressure applied by the patient onto probe 110 or vice versa (and transferred from probe 110 to holder 122). Base unit 140 may determine if the pressure reading is within an acceptable range (e.g., a range that indicates probe 110 is in contact with the patient, but not applying excessive force).

If the probe holder pressure is not within the threshold window (block 730—No), process 700 may include adjusting the probe holder height (block 735). For example, base unit 140 may cause a height adjustor (e.g., height adjustor 514) to increase or decrease the height of probe holder 122 to achieve an acceptable pressure level.

After the height of probe holder 122 is adjusted, or if the probe holder pressure is within the threshold window (block 730—Yes), process 700 may include causing the probe to transmit ultrasound signals at the first increment or location (block 740), recording a linear position and height of the probe holder at the first increment (block 745), and receiving echo information associated with the transmitted ultrasound signals (block 750). For example, base unit 140 may confirm that probe holder 122 is in the correct first position and activate probe 110 to transmit ultrasound signals. Probe 110 may transmit ultrasound signals and receive echo data, which may be relayed or sent back to base unit 140. Base unit 140 may associate the linear position (e.g., increment marker 428) and height position (e.g., position of height adjustor 514) of probe holder 122 with the received echo information.

Process 700 may further include determining if there are more increments at which to scan (block 755). For example, based on the technician input of block 720, base unit 140 may determine if addition scans at the various incremental locations are required to complete the assigned linear distance.

If there are more scans to perform (block 755—Yes), process 700 may return to process block 725 to move the probe holder to the next location/increment. If there are no more increments or portions to scan (block 755—No), the received echo information may be processed as a 3D ultrasound image (block 760). For example, base unit 140 may receive echo data, collected along the various known locations of track structure 126 at which scans were performed, to generate 2D B-mode image data to determine a size of a vessel (such as an aneurysm in the abdominal aorta). In other implementations, echo data from probe 110 may be processed to generate 3D image data.

FIG. 8 is a flow diagram illustrating an exemplary process 800 for identifying parameters or elements associated with a target of interest. According to an implementation, the process 800 may correspond to process block 760 of FIG. 7. In this example, assume that the target is the abdominal aorta. It should be understood that features described herein may be used to identify other vessels, organs or structures within the body.

In an exemplary implementation, a 3D shape model may be defined for a vascular structure (block 810). Generally, according to an exemplary implementation, the 3D shape model can be used to represent a patient's real vascular structure (e.g., an abdominal aorta) for quantitative analysis purposes. The simulated 3D shape model may be defined based on data from multiple comparable human structures. Possible variations can then be integrated into the shape model. For example, as shown in FIG. 10A-10F, a simulated 3D AAA shape model may be developed based on human abdominal aorta characteristics. Generally, the 3D AAA shapes in FIGS. 10A-10F may include structures representative of an aneurysm.

FIGS. 10A-10F represent six simulated 3D data sets 1010-1060, respectively, that may be used for a flexible shape model. Each of the 3D data sets 1010-1060 includes a top view (anterior-posterior, illustrated in the upper left frame), side view (transverse, illustrated in the upper right frame), and end view (illustrated in the lower left frame) of a simulated AAA structure.

The examples of FIGS. 10A-10F include blood vessels with different tortuosity embedded. Each of simulation shapes 1010-1060 may be derived from patient data (e.g., ultrasound data, CT scan data, MRI data, etc.) of normal and AAA conditions. While six simulation shapes 1010-1060 are shown in FIGS. 10A-10F, in other implementations more or fewer simulation shapes may be used for the flexible shape model.

Figure 11A:
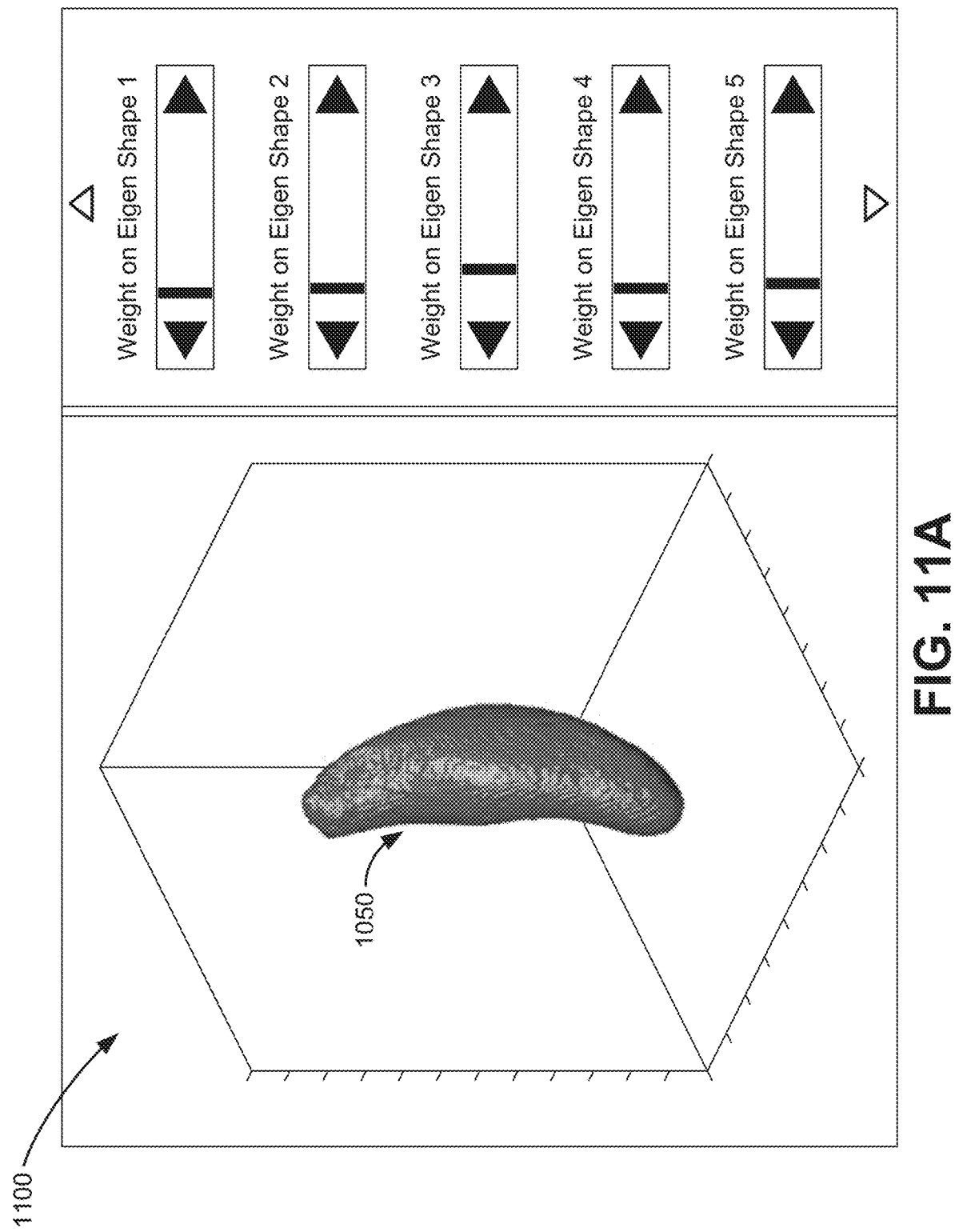
FIGS. 11A and 11B illustrate variations for a 3D shape model in accordance with the process of FIG. 8.
Figure 11B:
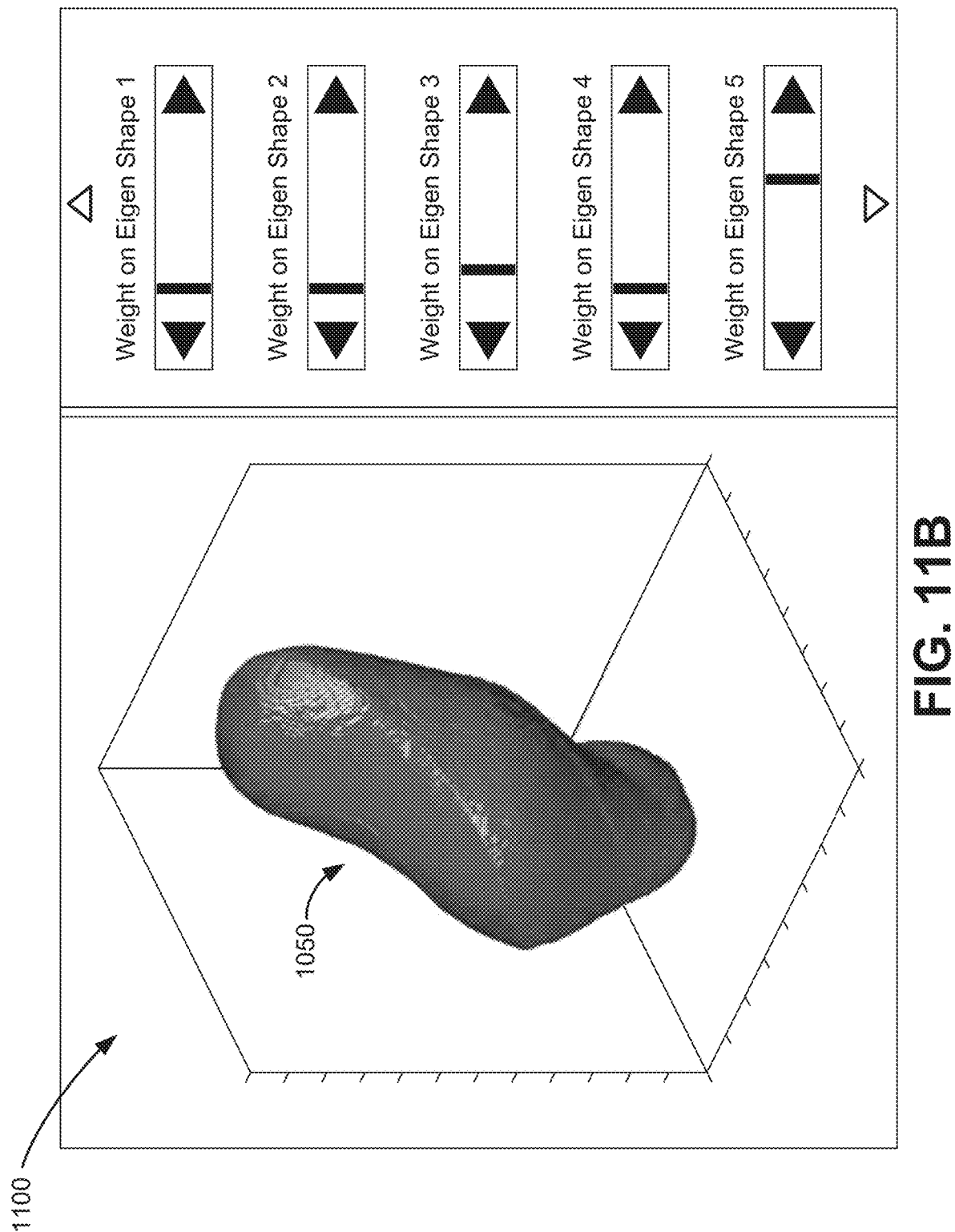

FIGS. 11A and 11B provide a simplified illustration a flexible shape model 1100. More particularly, FIGS. 11A and 11B illustrate how a simulation shape (e.g., simulation shape 1050) may be morphed or changed for shape fitting analysis. Other simulation shapes (e.g., 1010-1040 and 1060) may be modified in a similar manner. In the example of FIGS. 11A and 11B, the weighted value of a tortuous aneurysm off-center from a centerline (e.g., simulation shape 1050, corresponding to Eigen Shape 5 of FIGS. 11A and 11B) is increased from a relatively small weight in FIG. 11A to a larger weight in FIG. 11B (as illustrated via the slide bar located on the right side of FIGS. 11A and 11B). According to an exemplary implementation, the flexible shape model can "learn" from the training patterns of simulation shapes 1010-1060. The flexible shape model may provide a flexible representation without using specific contours or a mesh. The flexible 3D shape model is thus more resistant to noise or shadow than conventional techniques in 2D space. While FIGS. 11A and 11B show flexible shape model 1100 that may be manually adjusted using slide bars. In other implementations, flexible shape model 1100 may be selected/adjusted using a processor (e.g., processor 320) in probe 110 or base unit 140.

Referring back to FIG. 8, image data of a patient may be acquired (block 820). For example, in accordance with implementations described herein, probe 110 may collect scan data for a region of interest using track structure 120. Track structure 120 may be attached to an application-specific track stand 130 and may be controlled by base unit 140 to collect a series of 2D scans (or 'slices'). By the adjusting motor stepping size, a technician may control the slice thickness. By adjusting total step number, a technician can control the linear movement range. According to an implementation, the 2D image resolution can also be configured by the probe API.

Returning to process 800 of FIG. 8, process 800 may include performing image enhancement and generating a target 3D image (block 830). For example, probe 110 or base unit 140 may apply a noise reduction process to the ultrasound image data. For example, data acquisition unit 210 may receive a B-mode ultrasound image from probe 110 and apply noise reduction and/or other pre-processing techniques to remove speckle and background noise from the image. In some embodiments, the aspect ratio of the raw B-mode image can be adjusted through a resizing process to compensate for differences between axial and lateral resolution. In other implementations, such as when performing an abdominal aorta scanning application, a scan conversion and/or machine learning can also be applied to make the abdominal aorta shape closer to the expected or actual shape of an abdominal aorta (e.g., elongated as opposed to round). Base unit 140 (e.g., vessel/organ identification unit 220) may detect a region of interest, such as a concentration of dark pixels within the ultrasound image. The concentration of dark pixels may correspond to a vascular structure, such as the lumen of the abdominal aorta, which carries the blood through the abdominal aorta. Once a vascular structure is identified, vessel/organ identification unit 220 may generate a 3D data set. For example, 3D image data may be compiled based on B-mode scans along different linear increments.

Figure 12:
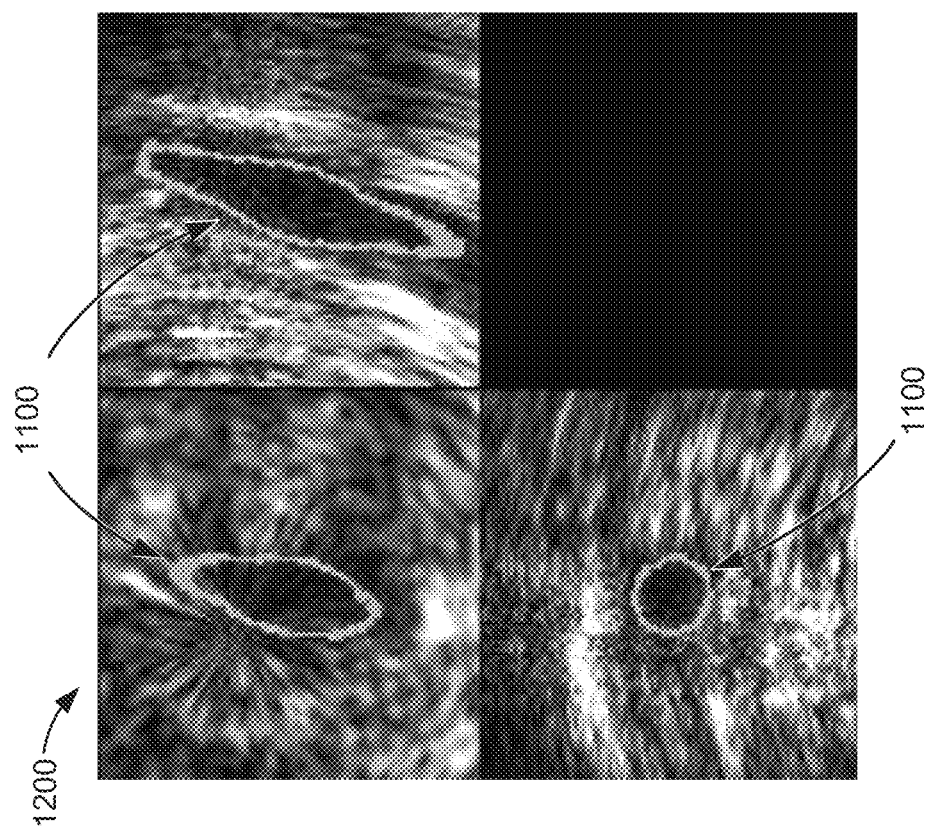
FIG. 12 illustrates applying a flexible 3D shape model to a target data set in accordance with an exemplary implementation.

As further shown in FIG. 8, process 800 may include fitting a flexible 3D aorta model onto the target 3D image (block 840). For example, the renderings of the incremental scans from probe 110 may be used together as a target 3D image data set to be matched to the flexible shape model (e.g., flexible shape model 1100). As illustrated in FIG. 12, segmentation unit 230 may overlay flexible shape model 1100 onto a target 3D image data set 1200 to determine a best fit. FIG. 12 is an illustration of an initial configuration of flexible shape model 1100 overlaid on target 3D image data set 1200. One or more different approaches to minimizing an energy functions may be used to fit shape model 1100 to a target 3D image data set (e.g., target image data set 1200). For example, resilient backpropagation (RPROP) is a learning heuristic for supervised learning in feedforward artificial neural networks. RPROP takes into account only the sign of the partial derivative over all patterns (not the magnitude), and acts independently on each "weight." For each weight, if there was a sign change of the partial derivative of the total error function compared to the last iteration, the update value for that weight is multiplied by a factor η−, where η−<1. If the last iteration produced the same sign, the update value is multiplied by a factor of η+, where η+>1. The update values are calculated for each weight in the above manner, and finally each weight is changed by its own update value, in the opposite direction of that weight's partial derivative, so as to minimize the total error function. In one implementation, η+ is empirically set to 1.1 and η− to 0.9.

Figure 13:
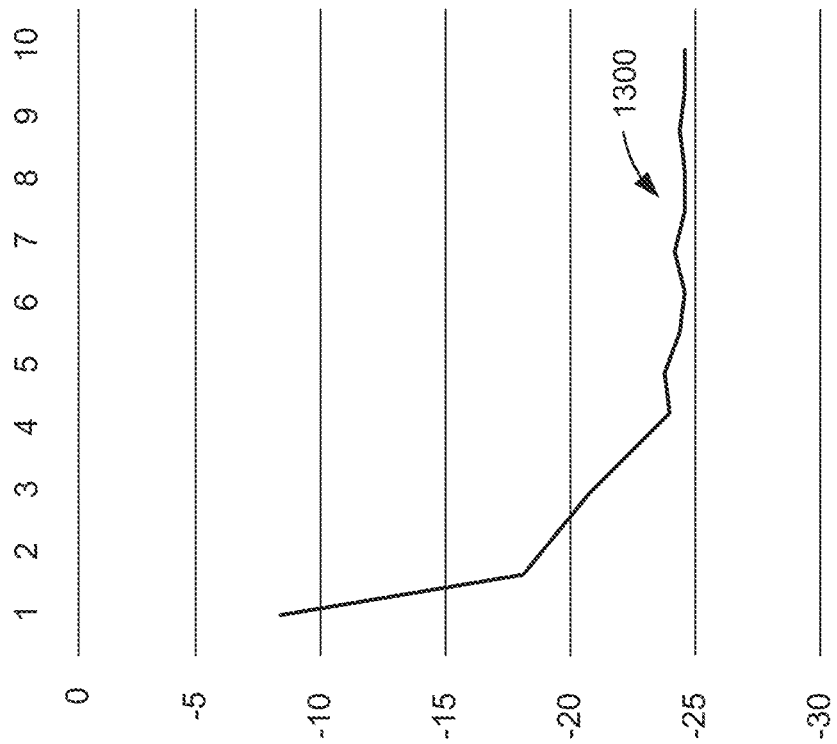
FIG. 13 is simplified energy changing curve that may correspond to minimizing an energy function for a flexible shape model over a target 3D image.

An energy function that may be used to fit shape model 1100 to a target 3D image data set is a data-driven statistical shape model. The data-driven statistical shape model may be more robust to the initialization and robust to noise during the segmentation task. Given a set of aligned training shapes $\{\varphi_i\}i=1 \ldots N$, each of the shapes can be represented by their corresponding shape vector $\{\alpha_i\}i=1 \ldots N$. In this notation, the goal of statistical shape learning is to infer a statistical distribution $P(\alpha)$ from the training samples. In the example of FIG. 12, a modified flexible shape model 1100 is overlaid on target 3D image data set 1200. For example, using a data-driven statistical shape model flexible shape model 1100 may be conformed to the 3D shape of the target image. FIG. 13 shows an energy changing curve 1300 that may correspond to multiple iterations indicated on the X-axis to minimize the energy function for flexible shape model 1100 over target 3D image data set 1200.

While RPROP provides on example of an image processing and optimization method that may be used with a shape model. In other implementations, statistical shape modeling may be applied inside different frameworks. For example, a shape model may also be embedded in a deep learning framework (e.g., as part of vessel/organ identification unit 220).

Figure 14:
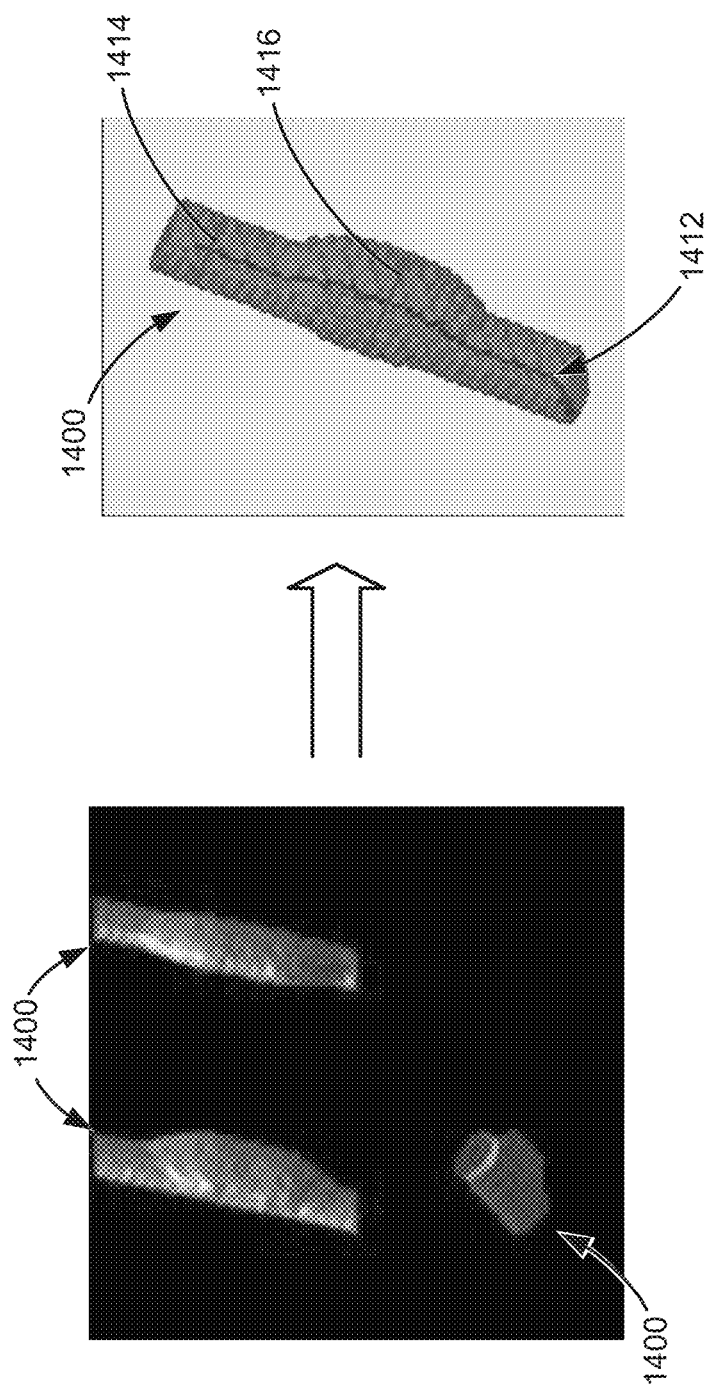
FIG. 14 is a diagram of a model, generated from a best-fit flexible shape model, to measure AAA characteristics.

Returning to FIG. 8, the best fit flexible shape model may be stored as a segmentation result (bock 850) and vascular measurements may be calculated using the stored segmentation result (block 860). For example, the best fit overlay corresponding to target 3D image data set 1200 (e.g., flexible shape model 1100 applied in FIG. 12) may be stored for quantitative analysis in an AAA evaluation by post processing unit 240. FIG. 14 illustrates a 3D (e.g., solid) model 1400 that may be generated from a best-fit flexible shape model 1100. With abdominal aorta segmentation available in the form of 3D model 1400, post processing unit 240 may determine size information for both the aorta and AAA, such as a centerline of the aorta 1412, the diameter of the aorta 1414, the maximum diameter of the aneurysm 1416, and the volume of the aneurysm. Since the AAA is not a tubular structure, the volume of the AAA and/or the ratio of the AAA area to the overall aorta may be a useful quantitative measure. In other implementations, post processing unit 240 may also determine the total area of the aorta and the diameter of the AAA. In each case, post processing unit 240 may output the size and/or area information via, for example, display 142. Using model 1400 for measurement and analysis enables post processing unit 240 to more easily identify the centerline of the aorta/AAA and determine the correct orientation for measuring the maximum abdominal aorta diameter (e.g., perpendicular to the centerline).

FIG. 9 is a flow diagram illustrating a process for a user to employ scanning system 100 to perform a ultrasound scan. Referring to FIG. 9, process 900 may include selecting a track stand for a scanning application (block 910), attaching the track stand to the track system (block 920), and positioning the track system and securing a probe in a probe holder of the track system (block 930). For example, based on the ROI of the patient (e.g., an abdominal aorta, vascular structure in a limb, etc.), a technician may select a track strand 130 suitable for a particular scanning application. The technician may attach the selected track stand 130 to track structure 120. For example, track stand 130 may be clipped, screwed, clamped, or latched onto track structure 120 and positioned over the necessary area of patient. Probe 110 may be secured within probe holder 122 to allow linear movement over the patient, such as shown in the configurations of FIG. 1, 5, or 6A-6C.

Process 900 may further include selecting a linear scan length (block 940), selecting a scanning increment (block 950), calibrating the probe orientation (block 960), and initiating a linear stage scan (block 970). For example, the technician may set a linear distance range (e.g., 3 inches to 24 inches) by providing input to an application running on base unit 140. The linear distance range may govern a start to end incremental scanning distance along a track (e.g., track 426, as measured from a first increment marker 428 to an ending increment marker 428). The technician may select a scanning increment, which may correspond to the step motor incremental advancement between actuation of a 2D scan by probe 110. For example, a selected increment may be every increment marker 428, every other increment marker 428, etc. The technician may calibrate the probe 110 installation in probe holder 122 to confirm the gyroscopic probe reading is consistent with the actual installed orientation and initiate the scanning procedure, using the scanning software, to jointly control the movement of track structure 120 and incremental actuation of probe 110 along track 126 to scan patent 150 at each location/increment.

As described above, scanning system 100 may use a conventional ultrasound probe that is mechanically guided to provide incremental scans over an area of interest. Scanning system 100 can be configured for different patient applications using interchangeable track stands. System 100 may also include at least one processing device configured to process the received echo information and generating a three-dimensional ultrasound image of the target blood vessel; obtain a flexible three-dimensional vascular model corresponding to the target blood vessel; identify a best-fit of the flexible three-dimensional vascular model onto the three-dimensional target image; store the best fit of the flexible three-dimensional vascular model as a segmentation result; and calculate, based on the segmentation result, measurements for the target blood vessel.

The foregoing description of exemplary implementations provides illustration and description, but is not intended to be exhaustive or to limit the embodiments to the precise form disclosed. Modifications and variations are possible in light of the above teachings or may be acquired from practice of the embodiments.

For example, features have been described above with respect to identifying a target of interest, such as a patient's abdominal aorta and AAA to estimate the size of the target (e.g., the aorta and/or the AAA). In other implementations, other vessels, organs or structures may be identified, and sizes or other parameters associated with the vessels, organs or structures may be estimated. For example, the processing described herein may be used to identify and display a bladder, prostate gland, a kidney, a uterus, ovaries, a heart, etc., as well as particular features associated with these targets, such as area-related measurements.

Further, while series of blocks have been described with respect to FIGS. 7-9, the order of the acts may be different in other implementations. Moreover, non-dependent blocks may be implemented in parallel.

It will be apparent that various features described above may be implemented in many different forms of software, firmware, and hardware in the implementations illustrated in the figures. The actual software code or specialized control hardware used to implement the various features is not limiting. Thus, the operation and behavior of the features were described without reference to the specific software code—it being understood that one of ordinary skill in the art would be able to design software and control hardware to implement the various features based on the description herein.

Further, certain portions of the invention may be implemented as "logic" that performs one or more functions. This logic may include hardware, such as one or more processors, microprocessor, application specific integrated circuits, field programmable gate arrays or other processing logic, software, or a combination of hardware and software.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

All structural and functional equivalents to the elements of the various aspects set forth in this disclosure that are known or later come to be known to those of ordinary skill in the art are expressly incorporated herein by reference and are intended to be encompassed by the claims. No claim element of a claim is to be interpreted under 35 U.S.C. § 112(f) unless the claim element expressly includes the phrase "means for" or "step for."

What is claimed is:

1. A system, comprising:
    a probe configured to:
        transmit ultrasound signals directed to a body part of a patient, and
        receive echo information associated with the transmitted ultrasound signals;
    a track structure including:
        a probe holder to secure the probe,
        a track frame that forms a linear path for the probe holder, and
        multiple interchangeable track stands configured to be removably attached to the track frame and support the track frame on the patient, wherein each of the multiple interchangeable track stands is configured to support the track frame in a position parallel to an extended target for a different body part application; and
    at least one processing device in a base unit, the at least one processing device configured to:
        communicate with the probe to obtain an installed rotational orientation of the probe with respect to the track frame and confirm that a gyroscopic reading of the probe is consistent with the installed rotational orientation;
        detect movement of the probe holder at increments along the track frame,
        actuate the probe to transmit the ultrasound signals at each of the increments and receive the echo information associated with each of the increments, and
        process the received echo information to generate a three-dimensional ultrasound image of the extended target based on a linear position of the probe holder at each increment.

2. The system of claim 1, wherein each of the interchangeable track stands includes an adjustable height guide to permit mounting the track frame at a preferred orientation.

3. The system of claim 2, wherein the multiple interchangeable track stands include application-specific track stands for scanning:
    a human abdomen, and
    a human leg.

4. The system of claim 1, wherein the track structure further includes:
    a pressure sensor, and
    a height adjustor,
    wherein the at least one processing device is further configured to adjust a relative height of the probe holder based on a reading from the pressure sensor.

5. The system of claim 4, wherein the at least one processing device is further configured to record the relative height of the probe holder at each increment, and
    wherein, the at least one processing device is further to process the received echo information based on a height position of the probe holder at each increment.

6. The system of claim 1, wherein the at least one processing device is further configured to record a linear position of the probe holder at each increment.

7. The system of claim 1, wherein the at least one processing device is further configured to:
    obtain a three-dimensional model corresponding to the extended target, wherein the three-dimensional model includes a statistical shape model that infers a statistical distribution and is derived from human samples,
    identify a best-fit of the three-dimensional model onto the three-dimensional ultrasound image,
    store the best fit of the three-dimensional model as a segmentation result, and
    calculate, based on the segmentation result, a measurement for the extended target.

8. The system of claim 1, wherein the track structure further includes:
    a motor to move the probe holder along the track frame, wherein the motor includes a stepping size that can be adjusted by a user to control a thickness of two-dimensional image slices processed by the at least one processing device, and
    wherein the probe holder includes a rotational probe holder configured to hold the probe in different rotational orientations.

9. The system of claim 1, wherein the at least one processing device is further configured to:
    determine a longitudinal centerline of the extended target based on the three-dimensional ultrasound image.

10. The system of claim 1, further comprising:
    a gel dispenser connected to the probe holder, wherein the gel dispenser automatically ejects gel onto the patient near a tip of the probe.

11. A method performed by a system including a track structure, an ultrasound probe, and a base unit that controls the track structure and the ultrasound probe, the method comprising:
receiving, on the track structure, one of multiple interchangeable application-based track stands to support the track structure and the ultrasound probe over an area of interest on a patient;
holding the ultrasound probe, positioned in contact with a patient, in a probe holder of the track structure;
communicating with the ultrasound probe to obtain an installed rotational orientation of the ultrasound probe with respect to the track structure and confirm that a gyroscopic reading of the ultrasound probe is consistent with the installed rotational orientation;
detecting movement of the probe holder at increments along the track structure;
causing the ultrasound probe to transmit ultrasound signals at each of the increments;
recording a linear position of the probe holder at each of the increments;
receiving echo information associated with the transmitted ultrasound signals; and
processing the received echo information to generate a three-dimensional ultrasound image of the extended target based on the received echo information and the linear positions of the probe holder,
wherein processing the received echo information includes:
obtaining a three-dimensional model corresponding to the extended target, wherein the three-dimensional model includes a statistical shape model that infers a statistical distribution and is derived from human samples, and
identifying a best-fit of the three-dimensional model for the three-dimensional ultrasound image by minimizing an energy function.

12. The method of claim 11, wherein each of the interchangeable track stands includes an adjustable height guide to permit mounting the track frame at a preferred orientation relative to the patient.

13. The method of claim 11, further comprising:
receiving user input to define a stepping size for the motor to move the probe holder along the track frame; and
receiving user input to define a linear distance for an incremental scan.

14. The method of claim 11, further comprising:
receiving a pressure reading, associated with the probe holder, at each of the increments;
adjusting a height of the probe holder based on the pressure reading; and
recording a height position of the probe holder at each increment.

15. The method of claim 11, further comprising:
storing the best fit of the three-dimensional model as a segmentation result, and
calculating, based on the segmentation result, a measurement for the extended target.

16. The method of claim 15, wherein the extended target is an abdominal aorta, and wherein calculating the measurements for the extended target comprises:
determining a longitudinal centerline of the abdominal aorta based on the three-dimensional model.

17. The method of claim 16, wherein calculating the measurements for the extended target further comprises:
determining a maximum diameter of at least one of the abdominal aorta or an abdominal aortic aneurysm, wherein the maximum diameter is measured perpendicularly to the longitudinal centerline.

18. A non-transitory computer-readable medium having stored thereon sequences of instructions which, when executed by at least one processor, cause the at least one processor to:
communicate with an ultrasound probe to detect an installed orientation of the ultrasound probe secured with respect to a track structure and confirm that a gyroscopic reading of the ultrasound probe is consistent with the installed rotational orientation of the ultrasound probe installed in a probe holder of the track structure;
detect movement of the probe holder at increments along the track structure;
cause the ultrasound probe to transmit ultrasound signals at each of the increments while in contact with a patient;
record a linear position of the probe holder at each of the increments;
receive echo information associated with the transmitted ultrasound signals; and
process the received echo information to generate a three-dimensional ultrasound image of an extended target based on the received echo information and the linear positions of the probe holder,
wherein processing the received echo information includes:
obtaining a three-dimensional model corresponding to the extended target, wherein the three-dimensional model includes a statistical shape model that infers a statistical distribution and is derived from human samples,
identifying a best-fit of the three-dimensional model for the three-dimensional ultrasound image by minimizing an energy function,
storing the best fit of the three-dimensional model as a segmentation result, and
calculating, based on the segmentation result, a longitudinal centerline for the extended target.

19. The non-transitory computer-readable medium of claim 18, wherein the instructions further cause the at least one processor to:
receive a pressure reading, associated with the probe holder, at each of the increments;
adjust a height of the probe holder based on the pressure readings; and
record a height position of the probe holder at each increment.

20. The non-transitory computer-readable medium of claim 19, wherein the instructions further cause the at least one processor to:
process the received echo information to generate a three-dimensional ultrasound image of the extended target based additionally on the recorded height position of the probe holder at each increment.

* * * * *